United States Patent [19]

Allington

[11] Patent Number: 4,869,374
[45] Date of Patent: Sep. 26, 1989

[54] CHROMATOGRAPHIC PUMPING SYSTEM

[75] Inventor: Robert W. Allington, Lincoln, Nebr.

[73] Assignee: Isco, Inc., Lincoln, Nebr.

[21] Appl. No.: 99,387

[22] Filed: Sep. 21, 1987

Related U.S. Application Data

[62] Division of Ser. No. 838,295, Mar. 10, 1986, Pat. No. 4,733,152.

[51] Int. Cl.$^4$ ............................................. B01D 15/08
[52] U.S. Cl. .................................. 210/198.2; 210/101; 417/45
[58] Field of Search ............... 210/741, 657, 659, 101, 210/198.2; 417/18, 45

[56] References Cited

U.S. PATENT DOCUMENTS

| | | | |
|---|---|---|---|
| 4,043,906 | 8/1977 | Helmer | 210/198.2 |
| 4,128,476 | 12/1978 | Rock | 210/198.2 |
| 4,422,942 | 12/1983 | Allington | 210/659 |
| 4,595,495 | 6/1986 | Yotam et al. | 210/198.2 |
| 4,752,385 | 6/1988 | Wilson | 210/656 |

Primary Examiner—Ernest G. Therkorn
Attorney, Agent, or Firm—Vincent L. Carney

[57] ABSTRACT

To provide smooth constant flow from a pump, a chromatographic system comprises: a chromatographic column having an inlet; a pump for supplying fluid to the inlet of the chromatographic column; a power means for the pump motor; positive and negative feedback loop means for controlling said power means; means for energizing and said positive and negative feedback control means; said negative feedback control means receiving a signal from said means for measuring flow rate and including means for comparing said signal with said corrected flow rate reference signal while said second feedback loop is energized to generate an error signal controlling said power means; and said positive feedback control means applying an acceleration voltage to said motor from a time a preset period after the initiation of a return stroke of said piston until after a timed duration.

24 Claims, 11 Drawing Sheets

CHROMATOGRAPHIC PUMPING SYSTEM

This application is a division of application Ser. No. 838,295, filed Mar. 10, 1986, now U.S. Pat. No. 4,733,152.

BACKGROUND OF THE INVENTION

This invention relates to reciprocation pumps and control circuits for them.

In one class of reciprocating pump, a piston continuously reciprocates in a cylinder to directly force a liquid from the cylinder, alternately pulling liquid into the cylinder through an inlet port from a reservoir and pushing it from the cylinder through an outlet port to the destination of the liquid.

In some uses of this class of pump, the pumps are designed to reduce pulsation in the flow of fluid. One such use is liquid chromatography. It is desirable in liquid chromatography that liquid which is pumped through a chromatographic column flow at a constant flow rate through the column so that different molecular species in the effluent from the column are eluted at times that are reproducible from run to run. Pulses in which the liquid flows at unpredictable rates reduce this reproduciblity.

In one type of prior art pump of this class, the pressure at the outlet port of the pump is measured by a pressure sensor. A feedback signal from the pressure sensor controls the speed of the pump motor to cause the pump motor to react to changes in pressure in the chromatographic column and thus maintain a more constant rate of flow of the fluid. One pump of this type is described in U.S. Pat. No. 3,985,467, issued Oct. 12, 1976 to Peter Lefferson.

This type of pump has a disadvantage when used in liquid chromatography in that it maintains pressure constant against varying pressure loads but may cause the rate of flow of fluid through the chromatographic column to vary, even in applications where is is desirable to maintain the rate of flow of liquid constant.

In another type of prior art pump of this class, the piston is driven at a constant rate while expelling liquid from the pump into the chromatographic column, but when returning on a fill stroke to draw fluid into the pump from the reservoir, the motor is driven at an increased and substantially constant speed to draw the fluid into the pump more rapidly.

During the forward stroke of piston in this type of prior art pump, the piston moves at a higher than normal rate until the pressure in the pump cylinder equals the pressure that existed near the end of the liquid expelling forward stroke of the piston and just before the piston began a refill stroke. After the pressure in the cylinder reaches the pressure during constant flow rate pumping before the start of the refill stroke, the outlet valve is opened and the piston continues forward at a constant rate. This type of pump is described in U.S. Pat. No. 4,131,393 issued Dec. 26, 1978, to Haaken T. Magnussen Jr. and 4,180,375 issued Dec. 25, 1979 to Haaken T. Magnussen Jr.

This type of pump has several disadvantages such as for example: (1) the opening of the valve at the pressure of the last part of the previous cycle results in an increased time during which no liquid leaves the outlet port over that time needed to fill the cylinder; and (2) the constant speed of the motor during refill and pump up does not reduce the time before fluid leaves the pump as soon as it could.

SUMMARY OF THE INVENTION

Accordingly, it is an object of this invention to provide a novel pump.

It is a further object of the invention to provide a novel method for pumping fluid in a manner that maintains a constant rate of flow of fluid through a chromatographic column spaced from the outlet of the pump.

It is a still further object of this invention to provide a pumping technique in which the speed of the motor is constant during a second portion of a pumping stroke until a refill portion of a cycle is initiated and then continuously increasing in speed during refill and until after a first portion of the pumping stroke controlled in time duration.

It is a still further object of this invention to drive a pump motor for a reciprocating pump at a constant rate during a first portion of a cycle with a feedback circuit and at an accelerating rate during a second portion controlled by a timer and an open loop control circuit.

It is a further object of the invention to maintain average rate of flow constant.

It is a still further object of this invention to provide a reciprocating pump for a chromatographic system in which the pump refill time is maintained as short as possible and liquid is pumped in such a manner as to prevent cavitation but increase the rate of flow of fluid temporarily to maintain as constant as possible from cycle to cycle the average amount of liquid pumped through the liquid chromatographic column.

It is a still further object of the invention to cause a smooth acceleration of pumping for a time after a refill stroke to reduce the danger of cavitation but maintain the flow rate at the column as constant as possible.

In accordance with the above and further objects of the invention, the speed of a motor which drives a direct displacement reciprocating pump is controlled by first and second related signals. These signals are related so that a high constant rate of pumping controlled by the first signal results in a long time of acceleration of the pumping action later under the control of the second signal to more quickly average the flow rate to the preset flow rate of the liquid after a refill portion of a pump cycle.

The first signal provides a linear feedback control on the pumping motion of a piston during a time period in which the rate of flow of liquid from the pump is equal to a present rate of flow and the piston moves at a preset velocity. The second signal is a nonlinear positive feedback signal which accelerates the motor linearly through an open loop to pull liquid from the liquid reservoir as fast as possible without cavitation and to provide liquid without cavitation to the outlet port of the pump at a rate to replace, in the conduit to the chromatographic column, the liquid necessary to bring the average rate of flow back to the preset value with little interruption to fill the cylinder. Thus, the piston is driven in a continuously varying rate except for a portion of a pump cycle.

A second feedback loop, within which the first and second signals operate, measures the flow rate from the pump and corrects the preset rate of flow current source to maintain the average flow rate over a pump cycle constant.

From the above description, it can be understood that the pump of this invention has several advantages such as: (1) the time during which no liquid is pumped through the outlet port is low; (2) it is relatively uncomplicated because the acceleration time of the motor is time limited rather than distance limited; (3) it is able to accommodate a wide range of flow rates without cavitation; (4) it maintains an accelerating velocity during a first part of each pumping stroke related to the required liquid to be replaced; and (5) it repeatedly monitors rate of flow and corrects the input signal outside of the feedback loop to aid in maintaining average flow constant.

SUMMARY OF THE DRAWINGS

The above noted and other features of the invention will be better understood from the following detailed description when considered with reference to the accompanying drawings in which.

DETAILED DESCRIPTION

Figure 1:
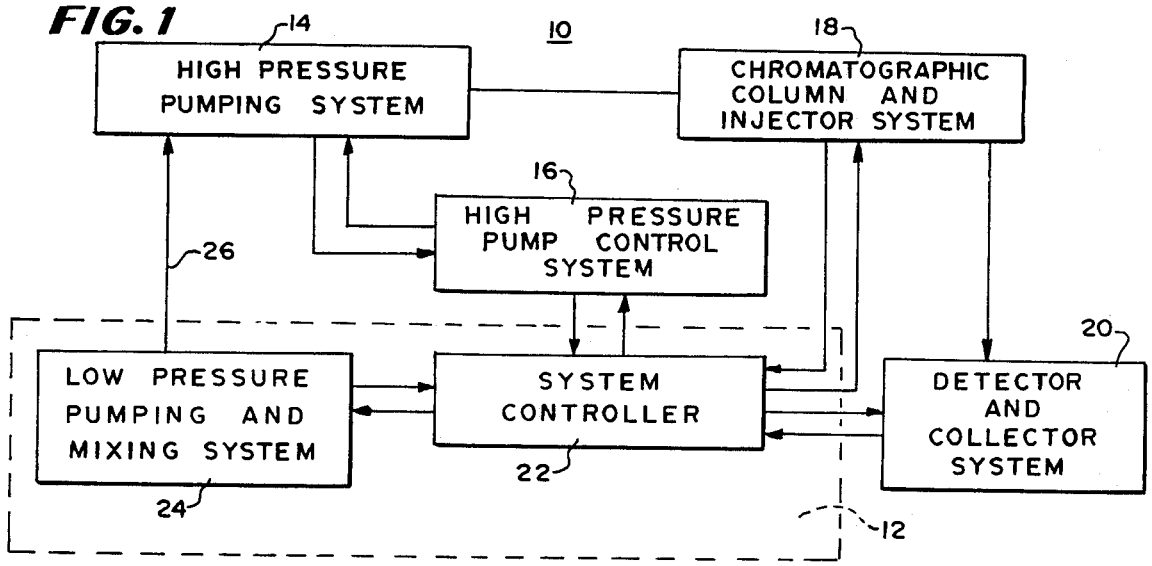
FIG. 1 is a block diagram of a chromatographic system utilizing an embodiment of the invention.

In FIG. 1, there is shown a block diagram of a chromatographic system 10, having a low pressure system 12, a high pressure pumping system 14, a high pressure pump control system 16, a chromatographic column, and injector system 18 and a detector and collector system 20. The high pressure pumping system 14 communicates with the low pressure system 12 to receive solvents therefrom and with the chromatographic column and injector 18 to supply the influent thereto for detection and at times collection by the detector and collector system 20.

To control the high pressure pumping system 14, the high pressure pump control system 16 is electrically connected to the low pressure system 12 from which it receives signals relating to flow rate of the influent to the chromatographic column and injector system 18 and is electrically connected to the high pressure pumping system 14 to maintain that flow rate as constant as possible.

The low pressure system 12, the chromatographic column and injector system 18 and the detector and collector system 20 are not part of this invention except insofar as they cooperate with the high pressure pumping system 14 and the high pressure pump control system 16 to provide a constant flow rate of solvents through the chromatographic column and injector system 18.

The low pressure system 12 includes a low pressure pumping and mixing system 24 and a general system controller 22. The general system controller 22 contains flow rate information and, in some configurations, gradient information as well as information for injecting samples into the chromatographis column or providing data acquisition and processing functions in conjunction with the detector and collector system 20. The general system controller 22 is not part of the invention except insofar as it provides signals to the high pressure pump control system 16 to control the flow rate from the high pressure pumping system 14.

Figure 2:
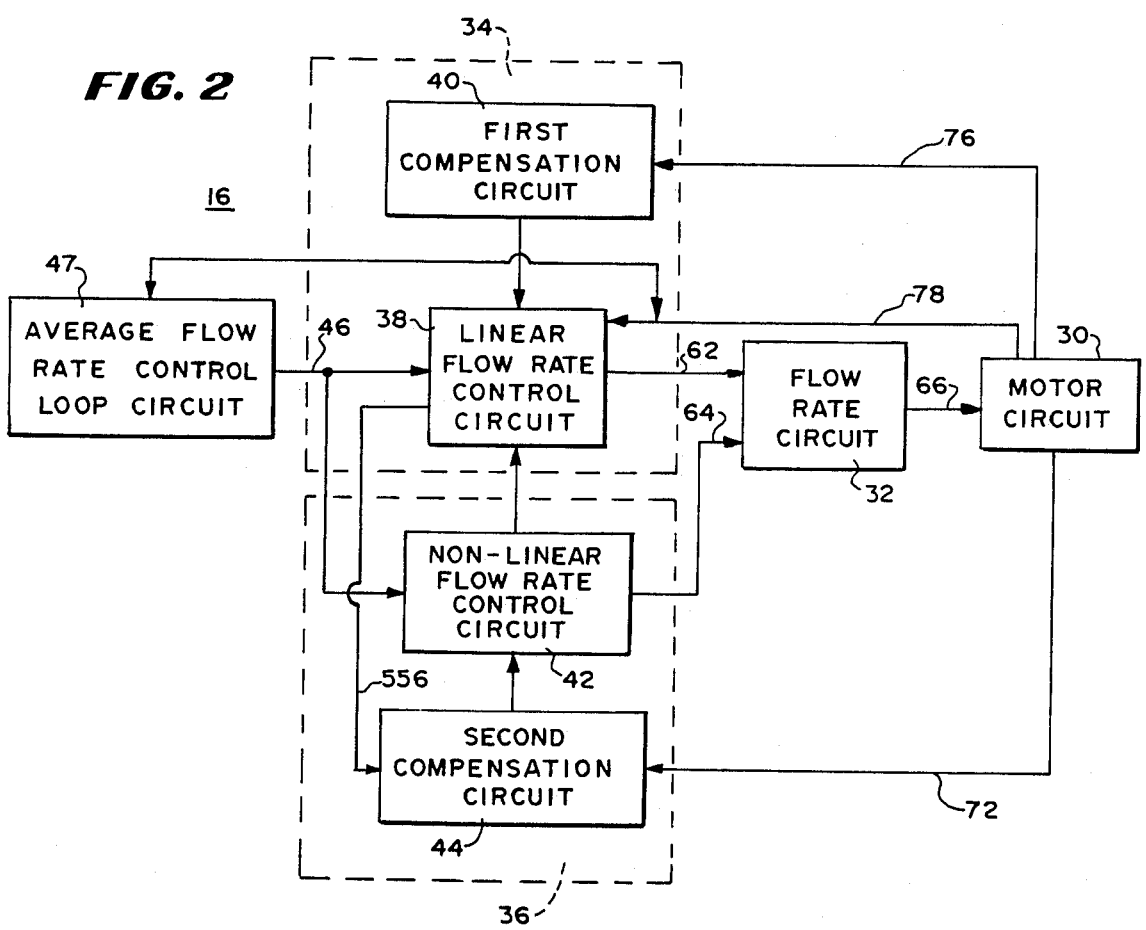
FIG. 2 is a block diagram of a control system for a high pressure pump in the chromatographic system of FIG. 1 in accordance with an embodiment of the invention.

In FIG. 2, there is shown a block diagram of the high pressure control system 16 having a motor circuit 30, a flow rate circuit 32, a first flow rate control system 34, a second flow rate control system 36 and an average flow rate control loop circuit 47. The first flow rate control system and the second flow rate control system each apply signals to the flow rate control circuit through conductors 62 and 64, one of them applying generally linear signals during at least a portion of each cycle of operation of the motor circuit and the other applying nonlinear signals through conductor 64.

The linear and nonlinear signals control a pulse-width-modulator within the flow rate circuit 32 which ultimately controls the speed of the motor circuit 30 to maintain the flow rate of the fluid through the chromatographic column and injector system 18 (FIG. 1) as nearly constant as possible. The linear and nonlinear signals are related, with the nonlinear signals being larger or smaller in relation to the linear signal and for this purpose the first flow rate control system and second flow rate control system are electrically connected through a conductor 556 in a manner to be described hereinafter. The average flow rate control loop circuit 47 periodically measures output liquid flow during each cycle of the pump and changes the signal on conductor 46 representing the preset flow rate to maintain an average flow rate equal to the preset flow rate.

To provide a substantially linear signal during at least a portion of the motor circuit 30, the first flow rate control system 34 includes a linear flow rate control circuit 38 and a first compensation circuit 40. The first compensation circuit 40 receives signals from the motor circuit 30 to provide certain correction signals to the linear flow rate control circuit 38 to which it is connected. The linear flow rate control circuit 38 receives signals from the system controller 22 (FIG. 1) on a conductor 46 indicating the desired rate of flow and supplies a resulting signals to the flow rate circuit 32 which includes corrections made in response to the motor circuit 30 and from the first compensation circuit 40.

To provide a signal to the flow rate control circuit 32 to accelerate the pump motor, the nonlinear flow rate control system 36 includes a nonlinear flow rate control circuit 42 and a second and positive feedback compensation circuit 44 (hereinafter second compensation circuit). The nonlinear flow rate control circuit 42 receives signals from the motor circuit 30 to which it is electrically connected and applies signals through an electrical connection to the flow rate circuit 32 as modified by signals from the second compensation circuit 44.

With this arrangement, the high pressure pump system 16 maintains the flow rate through the column relatively constant at the programmed rate to cause the time at which peaks are detected to be reproducible because of pulses of fluid of different rates occurring at different times in the column rather than constantly eluting the molecular species from the column. Generally, the high pressure pump control system 16 controls the pump motor through the motor circuit 30 in such a way as to maintain the average flow of fluid at the preset rate and minimize rapid fluctuations in flow rate such as might be caused by a refill stroke of a piston pump or the like.

Figure 3:
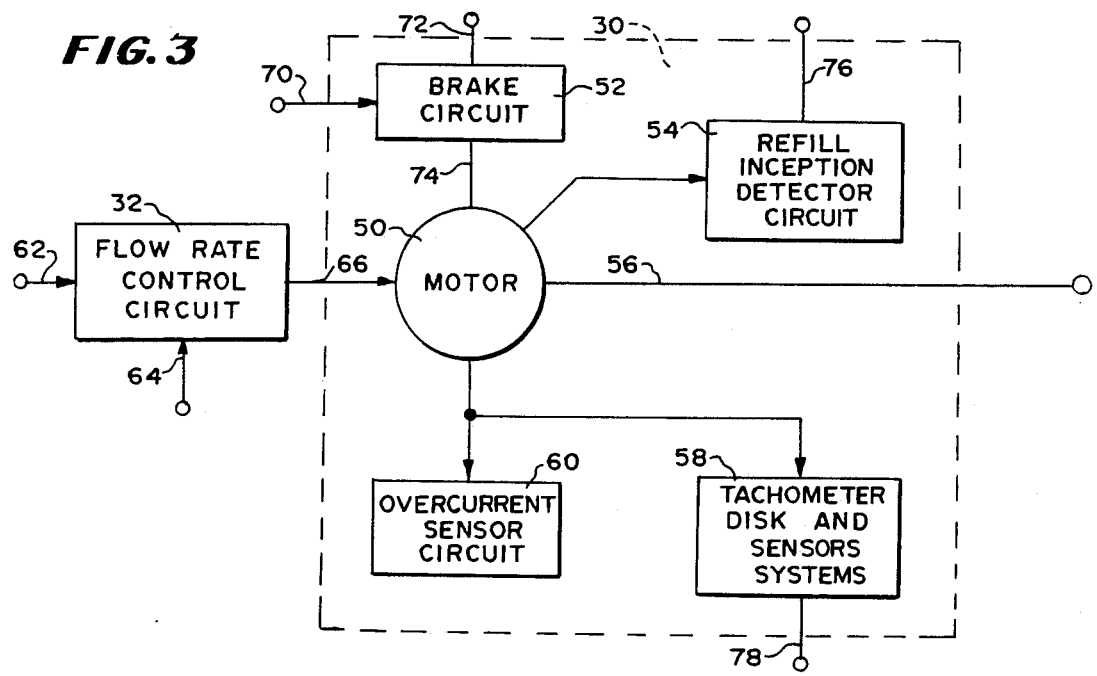
FIG. 3 is a block diagram of a motor circuit for a pump in accordance with the embodiment of FIG. 2.

In FIG. 3, there is shown a block diagram of the flow rate circuit 32 and the motor circuit 30. The flow rate control circuit 32: (1) receives a signal on conductor 62 during a portion of a pump cycle which is the output of a servo loop and has a substantially linear relationship with the desired pumping rate; and (2) a signal on conductor 64 which is a ramp nonlinearly corrected in slope to relate to the preset average flow rate. Both signals contain some corrections which are directed to establishing a rate of pumping which permits a single piston reciprocating pump to approach constant flow through a chromatographic column across a period of time.

The flow rate circuit 32 is electrically connected to the motor circuit 30 through a conductor 66 to apply to the motor circuit 30 periodic pulse-width-modulated signals in which the pulse width (duty cycle) is related to the speed at which the piston is intended to move to: (1) reduce flow rate pulsations in the chromatographic column by maintaining the average rate of flow of influent to the column is as constant as possible; and (2) change the piston speed to reduce the time that the pump is not forcing fluid through its outlet port. The speed of the piston is controlled to avoid cavitation or changes in the flow rate that are so sudden as to disrupt the rate of flow through the chromatographic column and injector system 18 (FIG. 1).

To provide a speed of piston movement for constant flow rate of the influent to the chromatographic column and injector system 18 (FIG. 1), the motor circuit 30 includes a motor 50, a brake circuit 52, a refill inception detector circuit 54, a tachometer disc and sensors system 58, and an overcurrent sensor circuit 60. The motor 50 is driven by power applied through the conductor 66 from the flow rate control circuit 32 and drives the piston of the pump (not shown in FIG. 3) through its outlet shaft 56.

To slow the pump, dynamic braking is under some circumstances applied to the motor through the brake circuit 52 in response to control signals on a conductor 70 indicating the time of application of the brake. The brake circuit 52 transmits signals through a conductor 72 to the first compensation circuit 40 (FIG. 2) which is used to adjust the motor speed at the end of a motor acceleration portion of a cycle to reduce drive power to the motor.

To aid in coordinating the pump motor control circuit within the second compensation circuit 44 (FIG. 2), the refill inception detector circuit 54 transmits a signal on conductor 76 for application to the first compensation circuit 40 (FIG. 2) at the end of a liquid delivery stroke to initiate a refill portion of a cycle. This signal aids in timing the start and termination of motor acceleration.

To generate signals indicating the volume of fluid pumped and motor speed, the tachometer disc and sensors system 58 generates signals for application through conductor 78 to the linear flow rate control circuit 38 (FIG. 2) and the average flow rate control loop circuit 47 (FIG. 2). The overcurrent sensor circuit 60 detects currents which exceed a preset value in the motor circuit, usually indicating binding or a bearing fault, so as to avoid damage to the pump.

Figure 4:
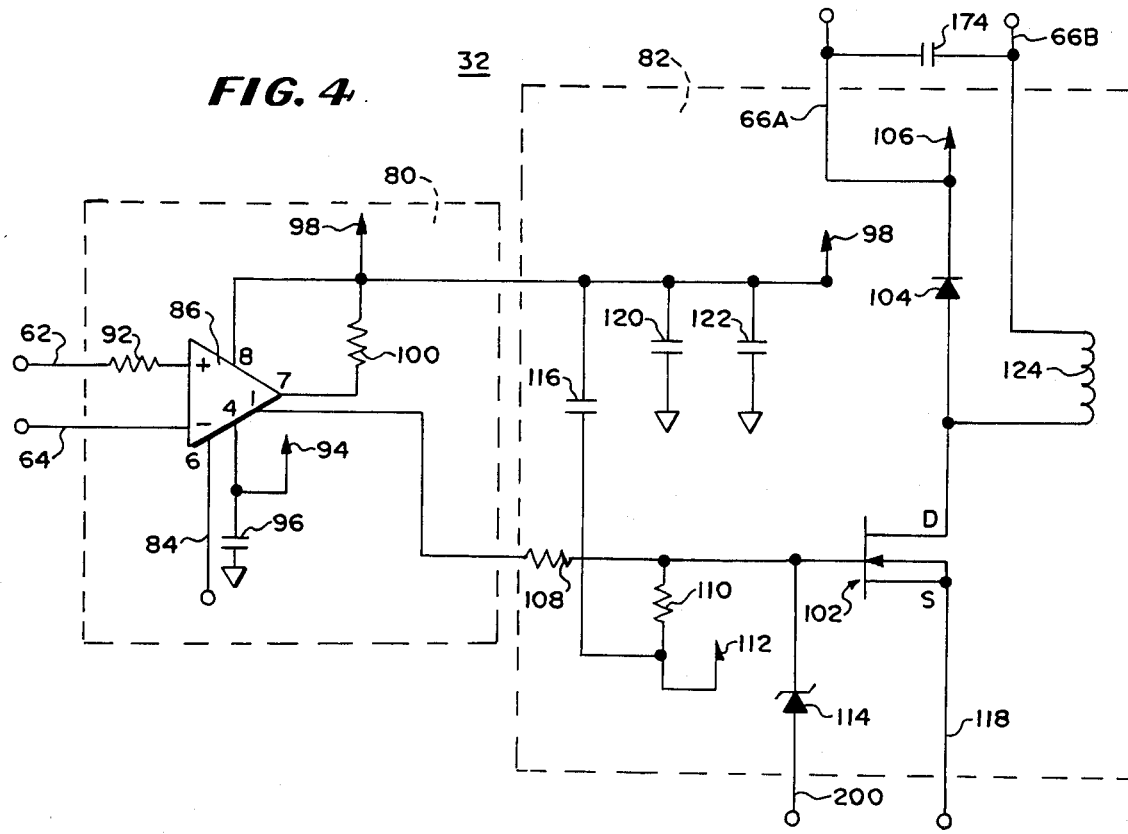
FIG. 4 is a schematic circuit diagram of a portion of the motor control circuit of FIG. 3.

In FIG. 4, there is shown a schematic circuit diagram of the flow rate circuit 32 having a comparator circuit shown generally at 80 and a driver circuit shown generally at 82, with the comparator circuit 80 receiving a ramp signal on conductor 64 from the second flow rate control system 36 (FIG. 2), a linear signal on conductor 62 from the first flow rate control circuit 34 (FIG. 2) and an overcurrent protection signal on conductor 84 from the second flow rate control system 36 (FIG. 2).

These signals result in an positive-going variable width 13 KHz (kilohertz) pulse train being applied by the comparator through a conductor to the drive circuit 82 inversely related to how steep the ramp circuit applied to conductor 64 is, and directly related to the amplitude of the signal applied to 62, which determines the duty factor of the pulse train.

The motor driver circuit 82, during the time duration it receives the pulse train from the comparator 80, applies a variable voltage across conductor 66A and 66B, resulting in power being applied to the motor 50 (FIG. 3) during a time controlled by the pulse-width-modulator 32 and consistent with the pulse train applied by the comparator 80.

To compare the ramp signal on conductor 64 with the servo input signal on conductor 62, the comparator circuit 80, is a LM 311 voltage comparator sold by National Semiconductor, 2900 Semiconductor Drive, Santa Clara, Calif. 25051, and described in its 1985 catalogue "Linear Integrated Circuits", having pin 1 electrically connected to the driver circuit 82, pin 2 electrically connected to conductor 62 through a 10K resistor 92 to receive the servo input signals, pin 3 electrically connected to conductor 64 to receive the ramp, a pin 4 electrically connected to a source 94 of a negative 12 volts and to the electrical common through a 1 uf (microfarad) capacitor 96, pin 6 electrically connected to conductor 84 to receive an overcurrent signal from the second flow rate control system 36 (FIG. 2) and pin 8 electrically connected to a source 98 of a positive 12 volts. An equivalent circuit would be a simple comparator having an inverter on its output connected to one input of a two input AND gate and conductor 84 connected to the other input.

The comparator 86 has its noninverting input terminal electrically connected to conductor 62 through the resistor 92 and its inverting input terminal electrically connected to conductor 64. A first rail is electrically connected to the source 94 of a minus 12 volts and to electrical common through the capacitor 96 and its other rail electrically connected to the source 98 of a positive 12 volts. The output of the comparator from pin 1 is electrically connected to the driver circuit 82 to apply a signal thereto corresponding to the time in which the ramp voltage applied on conductor 64 is less than the level on conductor 62.

The driver circuit 82, includes a MTP12N05 MOSFET transistor 102, a MR2400F diode 104 (all manufactured by Motorola Corporation), and a source 106 of a positive 32 volts. The gate of the transistor 102 is electrically connected: (1) to the output of the comparator 86 through a 33 ohm resistor 108; (2) to a source 112 of a negative 8 volts through a 820 ohm resistor 110; (3) to the overcurrent sensor circuit 60 (FIG. 3) through the reverse resistance of a 1N5245B Zener diode 114; and (4) to a source 98 of a positive 12 volts through the resistor 110.

The source of the transistor 102 is electrically connected to the overcurrent sensor circuit 60 (FIG. 3) through a conductor 118. To provide noise filtering for the comparator 86, the source 98 of a positive 12 volts is electrically connected to electrical common through two 1 uf capacitors 120 and 122 in parallel with each other and to the source 112 of a negative 8 volts through a 1 uf capacitor 116, with a source of negative volts 112 also being electrically connected to the gate through the resistor 110 to provide biasing directly to the gate. A 0.2 uf capacitor 174 is connected across conductors 66A and 66B to filter lower frequencies.

Conductor 118 is essentially grounded for power supply purposes and the drain is electrically connected through the forward resistance of the diode 104 to the source 106 of a positive 32 volts and to conductor 66A so that, the positive 32 volts is connected at all times to one end of the armature of the motor 50, (FIG. 3) conductor 66B on the other armature and being electrically connected through a current limiting inductor 124 to the anode of the diode 104 and the drain of the transistor 102. The capacitance across the motor is essentially 2 uf. The motor is a Pitman 13000 series DC motor and the inductor is substantially 200 uh (microhenries).

With this circuit arrangement, when the transistor 102 is conducting as a result of the positive pulse at its gate, current flows from the source 106 of a positive 6 volts through the motor, the inductor 124 and the transistor 102 to ground through conductor 118, and when the positive pulse is not applied, the current is maintained by inductor 124 through diode 104 and, the motor and back through the inductor unless the motor is operating to generate current for dissipation in the brake circuit 52 (FIG. 3) to be described hereinafter.

With this arrangement, when the linear feedback circuit indicates that the motor speed falls below its preset speed, the pulse width is increased linearly and when the nonlinear feedback circuit indicates the need for acceleration to equalize the flow, the width of the pulse is increased provide a correction of motor speed in a velocity feedback loop during a portion of a pump cycle prior to refill. The nonlinear feedback circuit provides an acceleration signal prior to the constant flow portion of the deliver for a longer time as the flow rate during the last portion of delivery increases and a shorter time as it decreases.

Figure 5:
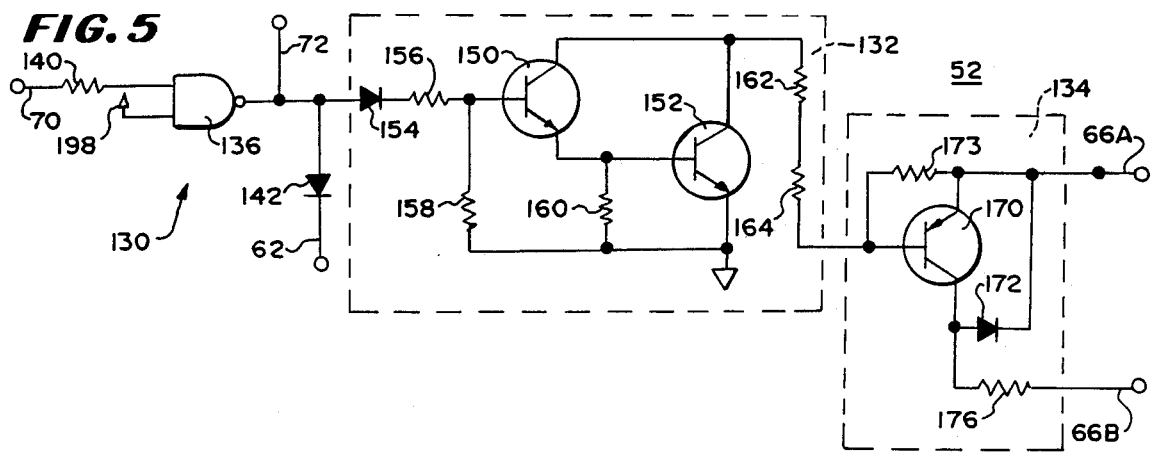
FIG. 5 is a schematic circuit diagram of another portion of the motor control circuit of FIG. 3.

In FIG. 5, there is shown a schematic circuit diagram of the brake circuit 52 (FIG. 3) having an input logic circuit 130, a drive circuit 132, and a shunt circuit 134. The input logic circuit 130 receives a signal on conductor 70 from the second flow rate correction circuit 36 (FIG. 2) and causes the drive circuit 132 to form a conducting path in the shunt circuit 134 across the armature of the motor to provide dynamic braking. The input logic circuit 130 also applies output signals through conductor 72 to the second compensation circuit 44 (FIG. 2) and to conductor 62 to the flow rate control circuit 32 (FIG. 3).

To provide a signal causing dynamic braking, the input logic circuit 130 includes a NAND gate 136, input conductor 70 and output conductor 72 and 62. The NAND gate 136 has one of its inputs electrically connected to a source 138 of a positive 8 volts and its other input electrically connected to the input 70 through a 10K resistor 140 to receive signals from the second flow rate correction system 36 (FIG. 2) indicating braking action. The output of the NAND gate 136 is electrically connected to conductor 72 to provide a positive output signal when braking action is to occur and to conductor 62 through the 1N5060 diode 142 to turn off drive pulses from the flow rate control circuit 32.

To energize the dynamic brake, the drive circuit 132 includes first and second NPN transistors 150 and 152 and a diode 154. The anode of the diode 154 is electrically connected to the output of the NAND gate 136 and its cathode is electrically connected to the base of the transistor 150 through a 4.7K (kilohm) resistor 156 and to electrical common through a 4.7K resistor 158. The emitter of transistor 150 is electrically connected to the base of transistor 152 and to electrical common through a 470 ohm resistor 160 and the emitter of transistor 152 is directly connected to electrical common. The collector of the transistors 150 and 152 are each electrically connected to the input to the shunt circuit 134 through two 39 ohm resistors 162 and 164 electrically connected in series. The transistors 150 and 152 are 2N3704 and D44C8 transistors manufactured by G.E. Corporation and described in the catalogue and the diode 154 is a type 1N914 diode.

To form a conducting path for current generated by the pump motor when it is being driven by inertia and thus to provide dynamic braking, the shunt circuit 134 includes a D45H8 PNP transistor 170, and a 1N5060 diode 172. The transistor 170 has its base electrically connected to the output of the drive circuit 132, its emitter electrically connected to its base through a 220 ohm pull-down resistor 173 and its collector electrically connected through the diode 172 to its emitter and to conductor 74B through a resistor 176.

The emitter of the transistor 170 is electrically connected to conductor 66A so that, when the motor operates as a generator for dynamic braking, a path is formed between conductors 66A and 66B through the motor and transistor 170 when transistor 170 is saturated and provides an open circuit when the motor is driven as a motor.

Figure 6:
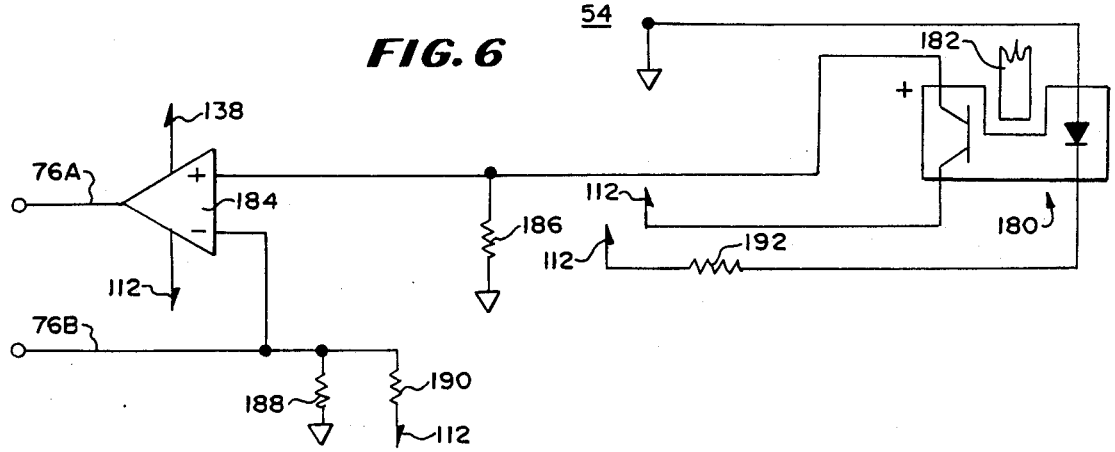
FIG. 6 is a schematic circuit diagram of still another portion of the motor control circuit of FIG. 3.

In FIG. 6, there is shown a schematic circuit diagram of the refill inception detection circuit 54 (FIG. 3), having an optical sensor 180, a rotatable flag 182 on the cam shaft, and a comparator 184. The flag 182 shown in fragmentary schematic form, rotates with the cam shaft on it in a location to be detected by the optical sensor 180, which transmits a positive going pulse in response to a signal indicating the start of the refill cycle to the noninverting input terminal of the comparator 184. The comparator 184 signals the second flow rate control system 36 (FIG. 2) indicating the start of the refill cycle in response to the detected signal.

For this purpose, the comparator 184 has its noninverting input terminal electrically connected to electrical common through a 2.2K resistor 186 and to the output of the optical sensor 180. The inverting input terminal of the comparator 184 is electrically connected to conductor 76B, to electrical common through a 100 ohm resistor 188 and to a source 112 of a negative 8 volts through a 1.5K resistor 190 so that a reference potential is established, above which a signal is provided through conductor 76A indicating a refill cycle. The comparator 184 has positive and negative 8 volt rails at 138 and 112.

The optical sensor 180 has a light emitting diode, with its anode electrically connected to electrical common and its cathode electrically connected to a source of negative 8 volts through a 1.5K resistor 192 and has a light sensitive transistor therein with its collector electrically connected to the noninverting input terminal of the comparator 184 and its NPN emitter junction electrically connected to the source 112 of a negative 8 volts.

Figure 7:
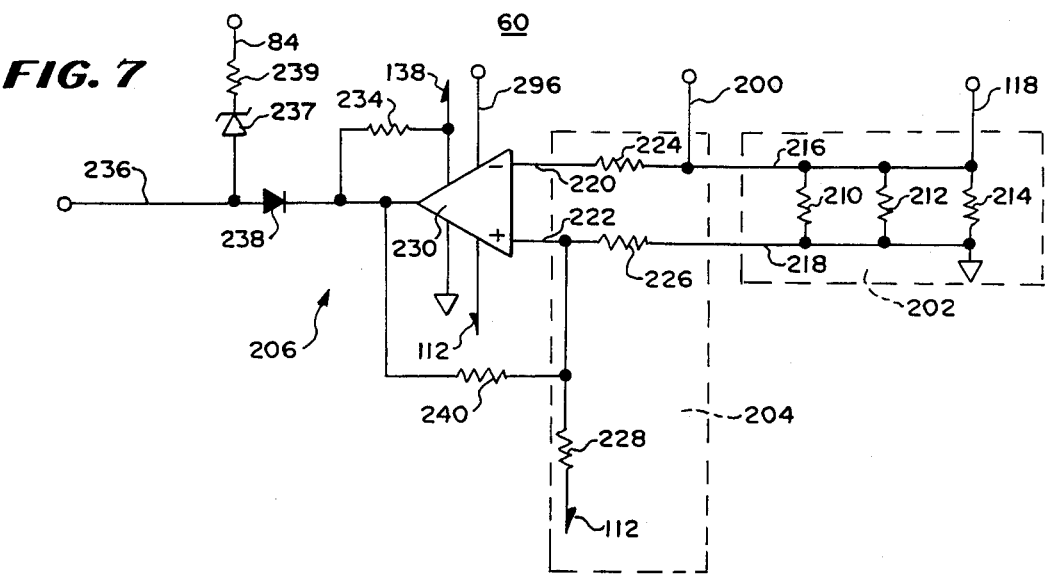
FIG. 7 is a schematic circuit diagram of still another portion of the motor control circuit of FIG. 3.

In FIG. 7, there is shown a schematic circuit diagram of the overcurrent sensor circuit 60 (FIG. 3) having a current sensing network 202, a reference network 204 and a comparator circuit 206. The sensing network 202 senses the motor current and the reference network 204 provides part of the reference with both values being compared in the comparator circuit 206 to provide an output signal disabling the flow rate control circuit 32 (FIG. 3 and FIG. 4) when the motor current is too high indicating a jammed condition of the pump or the like.

To sense the current through the pump, the current sensing network 202 includes three 0.1 ohm resistors 210, 212, and 214 respectively connected in parallel between a conductor 216 and a conductor 218. Conductor 216 is electrically connected to conductor 118 to receive motor current and conductor 218 is electrically connected to the electrical common so that the current flow through the motor on conductor 118 causes a voltage drop in the sensing network 202, which voltage drop occurs between conductors 216 and 218.

To provide a reference potential, the reference network 204 is electrically connected: (1) through 86.6K resistor 240 to 4.7K resistor 234 and thence to the source of a positive 8 volts; (2) to conductors 216 and 218; and (3) to the comparator circuit 206 through conductors 220 and 222. Conductor 216 is electrically connected through a conductor 200 to the anode of the Zener diode 114 (FIG. 4) of the flow rate control circuit 32 (FIG. 2, 3, and 4) to receive current therethrough and to conductor 220 through a 1K resistor 224. Conductor 218 is electrically connected to conductor 222 through a 4.75K resistor 226 and to a source 112 of a negative 8 volts potential through a 309K resistor 228. With this circuit arrangement, conductor 222 is maintained at a potential above the electrical common by the sources of potential 138 and resistors 234 and 240.

To compare the potential on conductors 220 and 222 for the purpose of indicating an overcurrent, the comparator circuit 206 includes the comparator 230 which is manufactured and sold by National Semiconductor Corporation (2900 Semiconductor Drive, Santa Clara, Calif. 95051) type 311 having its inverting input terminal at pin 3 electrically connected to conductor 220 and its noninverting input terminal at pin 2 electrically connected to conductor 222 to provide a comparison of the voltages therein.

During an overcurrent, the output at pin 7 of the comparator goes from 8 to common potential. The removes positive potential from resistor 240 and negative potential from sources 112 through resistor 278 causes the comparator to latch up and disable the motor drive circuit.

At the end of the pulse cycle, a reset pulse on pin 6 at 296 resets the comparator from a clock in the second positive feedback and compensation circuit 44 to enable the comparator and drive circuit 32.

The output of the comparator 230 at pin 7 is electrically connected to: (1) the source 138 through the resistor 234; (2) a conductor 84 through 680 ohm resistor 239; (3) the reverse resistance of the 8.2 IN5237 volt Zener diode 237 and the foreward resistance of diode 238; and (4) input conductor 222 through a 86.6K resistor 240. The conductor 84 (FIG. 4) is electrically connected to the pulse width modulator 86 (FIG. 4) so that conductor 84 provides signals to disable the flow rate circuit 32 (FIGS. 2, 3 and 4) by de-energizing the comparator 86 upon a current overload condition.

Figure 8:
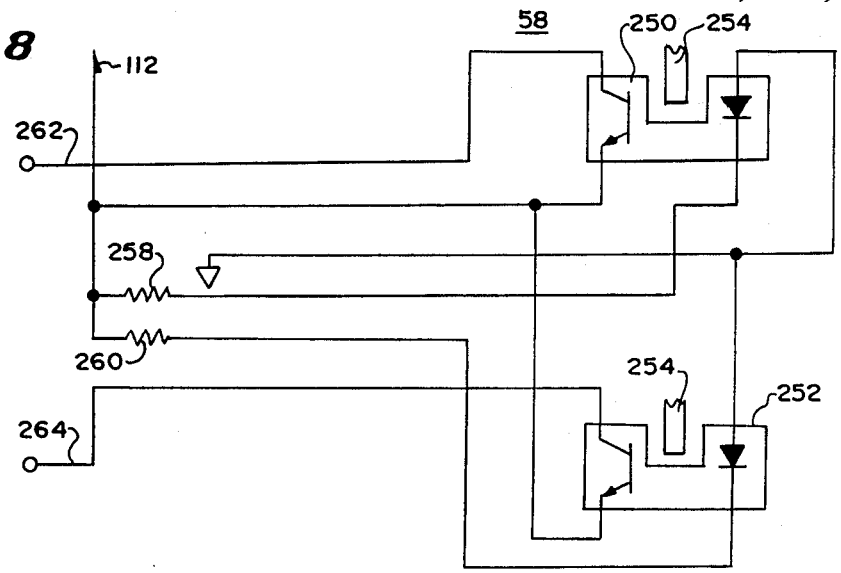
FIG. 8 is a schematic circuit diagram of another portion of the motor control circuit of FIG. 3.

In FIG. 8, there is shown a schematic circuit diagram of the tachometer disc and sensor system 58 (FIG. 3) having a first and a second optical sensor 250 and 252 respectively, rotatable disc 254 and first and second 270 ohm resistors 258 and 260 respectively. The first and second optical sensors sense indicia indicating the rotation of the pump on disc 254 which is mounted to the output shaft of the pump motor. The optical sensors 250 and 252 are located in quadrature with respect to the indicia so as to indicate the amount of rotation of the motor and its direction in a manner in the art.

With this arrangement, the optical sensors provide signals indicating the amount of rotation and direction of the motor by rotation of the disc in one direction as well as position of the piston in part of a delivery stroke by sensing indicia at equispaced distances along the disc 254. This type of circuit is described in U.S. copending application No. 713,328 to Robert W. Allington et al, assigned to the same assignee as this application and filed Mar. 18, 1985.

To sense indicia on disc 254 the first optical sensor 250 includes a light emitting diode having its anode electrically connected to the electrical common and its cathode electrcially connected to the source 112 of a negative 8 volts through the resistor 258. To provide electrical signals indicating the amount of electrical rotation of the disc 254, the first optical sensor 250 includes a light sensitive element separated from the light emitting diode by the disc 254 to have light blocked or transmitted to it as the disc 254 rotates.

The light sensitive element has its collector electrically connected to the linear flow rate control circuit 38 (FIG. 2) and nonlinear flow rate control circuit 42 (FIG. 2) and average flow rate control loop circuit 47 (FIG. 2) circuit 47 through a conductor 262 and has its emitter electrically connected to the source 112 of a negative 8 volts to provide electrical signals to a conductor 262 indicating the amount of rotation of the pump.

The second light sensor 252 has a light emitting diode in it with its anode electrically connected to the electrical common and its cathode electrically connected to the source 112 of a negative 8 volts through the 270 ohm resistor 260. It has a light sensitive element separated from the light emitting diode 252 by the rotatable disc 254 so as to sense indicia upon it.

The light sensitive element has its collector electrically connected to the linear and nonlinear flow rate control circuit 38 and 42 (FIG. 2) through a conductor 264 and average flow rate control loop circuit 47 (FIG. 2) and has its emitter electrically connected to the source 112 of a negative 8 volts so as to provide electrical signals to conductor 264 indicating the amount of rotation of the disc 254 with the signals on conductors 262 and 264 indicating the amount of rotation and the direction of rotation.

Figure 9:
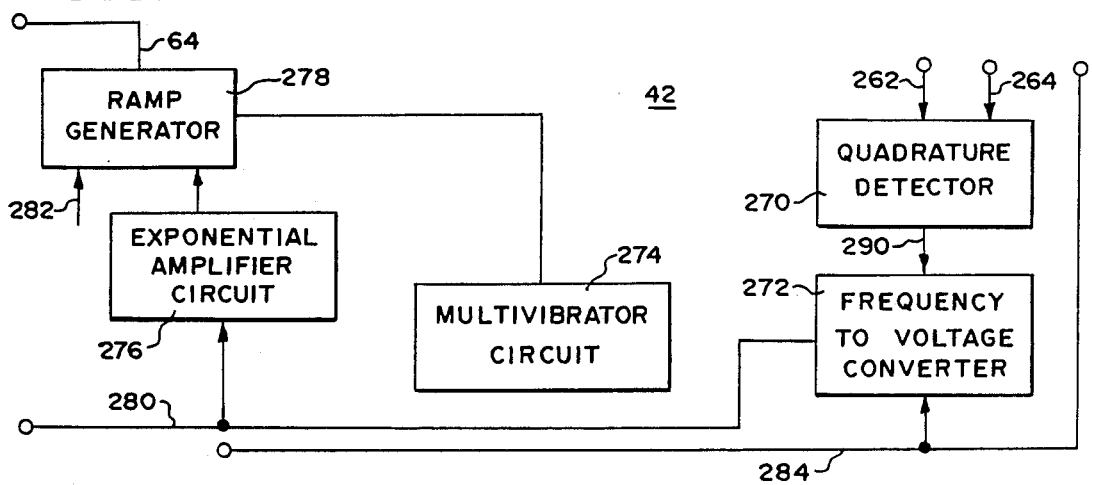
FIG. 9 is a block diagram of a portion of the circuit of FIG. 2.

In FIG. 9, there is shown a block diagram of the nonlinear flow rate control circuit 42 (FIG. 2) having a quadrature detector 270, a frequency to voltage converter 272, a multivibrator circuit 274, an exponential amplifier circuit 276 and a ramp generator 278. The quadrature detector 270 is electrically connected to conductors 262 and 264 to receive signals from the tachometer disc and sensor system 58 (FIGS. 3 and 8) and apply a signal indicating the amount of rotation in one direction to a conductor 290/frequency to voltage converter 272 which generates a signal representing in amplitude the rate of rotation of the motor for application to a conductor 280.

Conductor 280 is electrically connected to the exponential amplifier circuit 276 and the output from the exponential amplifier circuit 276 and from the multivibrator circuit 274 are connected to the ramp generator 278 to generate a ramp which varies in slope in a manner related to the motor speed.

To receive correcting signals, the second compensation circuit 44 (FIG. 2) is connected to the ramp generator 278 through a conductor 282 and to select the flow rate operating range of the frequency to voltage converter control signal is applied to the frequency to voltage converter 272 from the linear flow rate control circuit 38 (FIG. 2) through a conductor 284 to select a flow rate range.

Figure 10:
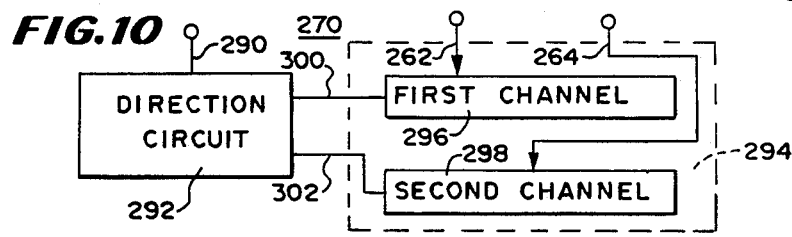
FIG. 10 is a block circuit diagram of one portion of the block diagram of FIG. 9.

In FIG. 10, there is shown a block diagram of the quadrature detector 270 (FIG. 9) having a pulse output conductor 290, a direction circuit 292 and a tachometer sensor input circuit 294. The tachometer sensor input circuit 294 is electrically connected to conductors 262 and 264 to receive signals from the first and second optical sensors 250 and 252 (FIG. 8) respectively, which sensors generate pulses at the same frequency as the motor rotates but 90 degrees out of phase. The output of the tachometer sensor input circuit 294 applies both sets of pulses to the direction circuit 292 which selects oly those pulses which indicate a forward movement of the pump piston or plunger for application to the output at conductor 290. This circuit is explained in the aforementioned patent application.

The tachometer sensor input circuit 294 includes a first channel 296 and a second channel 298 with the first channel 296 being electrically connected to the first optical sensor 250 through conductor 262 to recieve signals therefrom and electrically connected to the direction circuit 292 through a conductor 300 and the second channel 298 being electrically connected to the second sensor 252 (FIG. 9) through the conductor 264 to receive signals therefrom and to the direction circuit 292 through a conductor 302 to supply signals thereto. The first channel 296 is identical to the first channel 298 except that they receive signals from different sources and supply to the direction circuit 292 through different conductors.

Figure 11:
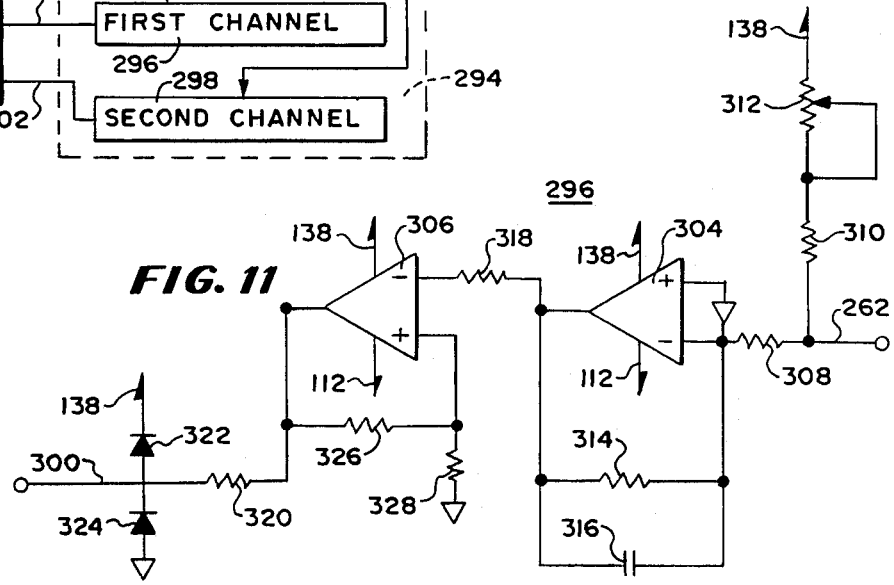
FIG. 11 is a schematic circuit diagram of a portion of the block diagram of FIG. 10.

In FIG. 11, there is shown a schematic circuit diagram of the first channel 296 (FIG. 10) within the tachometer sensor input circuit 294 (FIG. 10) having a first operational amplifier 304 and a second operational amplifier 306. The amplifiers 304 and 306 are type LM353 amplifiers each having one rail connected to a source 138 of a positive 8 volts and the other rail electrically connected to a source 112 of a negative 8 volts.

To provide amplification and low pass noise filtering, amplifier 304 has its noninverting input terminal electrically connected to the electrical common and its inverting input terminal electrically connected to: (1) conductor 262 through a 470 ohm resistor 308 and to a source 138 of a positive 8 volts through the resistor 308, a 27K resistor 310 and a variable 50K resistor 312 so as to permit adjustment of the input to operating current of the light sensor connected to conductor 262. The output of amplifier 304 is electrically connected to: (1) its inverting input terminal through a 56K resistor 314 and 150 pf (picofarad) capacitor 316 electrically connected in parallel; and (2) to the noninverting input terminal of the amplifier 304 through a 47K resistor 318.

To provide Schmidt trigger action, amplifier 306 has its output electrically connected to: (1) conductor 300 through a 4.7K resistor 320, a source 138 of a positive 8 volts through the resistor 320 and the forward resistance of a 1N273 diode 322; (3) and the electrical common through the reverse resistance of a 1N273 diode 324; (4) to its noninverting input terminal through a 1.2M resistor 326 and to the electrical common through the resistor 326 and a 47K resistor 328.

Figure 12:
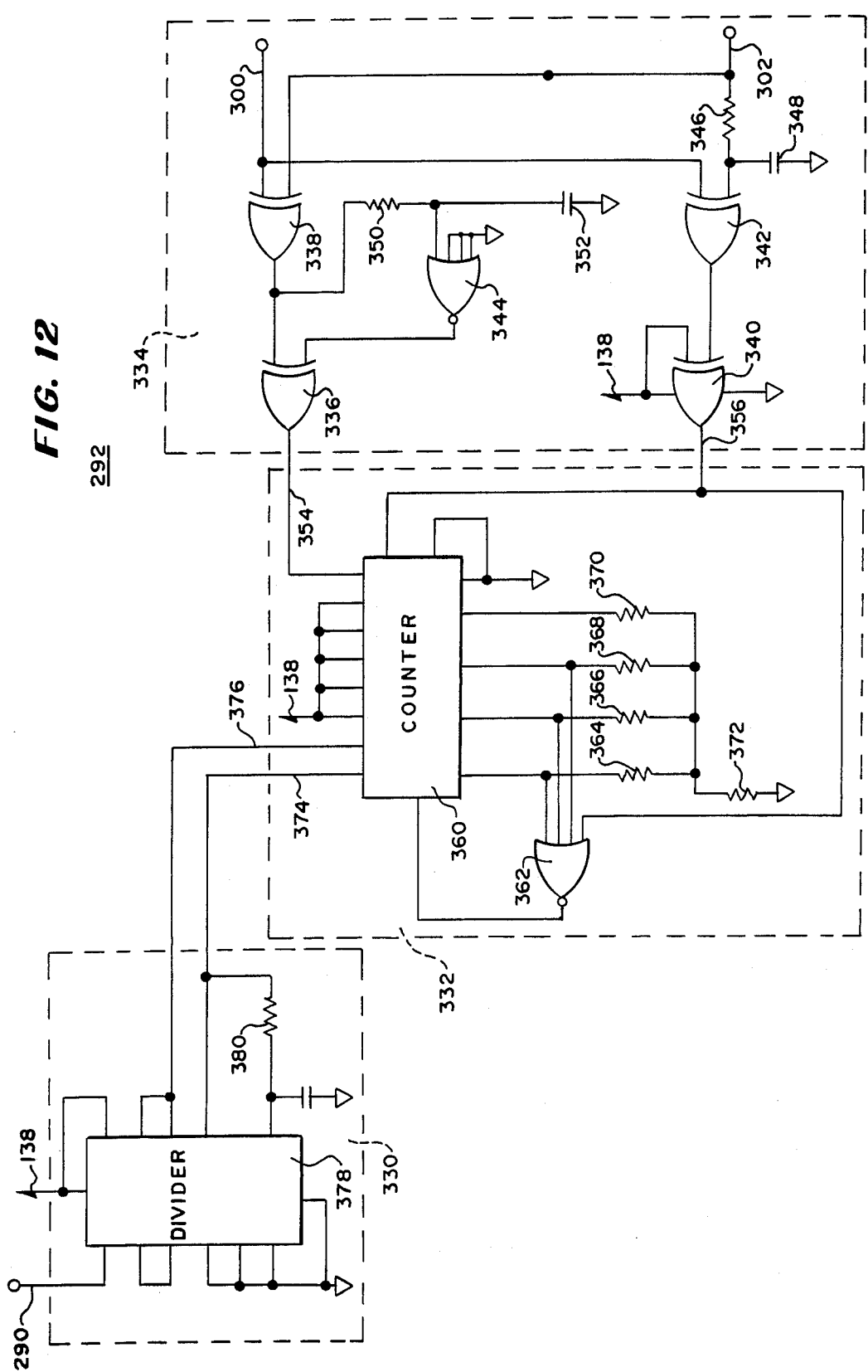
FIG. 12 is a schematic circuit diagram of another portion of the block diagram of FIG. 10.

In FIG. 12, there is shown a schematic circuit diagram of the direction circuit 292 (FIG. 10) having a divide-by-two circuit 330, an up-down counter circuit 332 and an input gating circuit 334. The input gating circuit 334 is electrically connected to conductors 300 and 302 to receive signals processed by channels 1 and 2 from the first and second sensors 250 and 252 respectively (FIG. 8) and has its output electrically connected to the up-down counter circuit 332 which caused by backward movement of counts pulses proportional to the motor, by counting backwards from 15 and requiring recounting of those pulses in the forward direction for application to the divide-by-two circuit 330 and eventually to output conductor 290 to the frequency to voltage converter 272 (FIG. 9).

The input gating circuit 334 includes four exclusive OR gates 336, 338, 340 and 342 and one NOR gate 344. Conductor 300 is electrically connected to one input of each of the exclusive OR gates 338 and and conductor 302 is electrically connected to another input of the two input exclusive OR gates 338 and 342 and to: (1) an input of the exclusive OR gate 342 through a 150K resistor 346; and (2) to the electrical common through the resistor 346 and a 120 pf capacitor 348. The output of exclusive OR gate 338 is electrically connected to: (1) one of the two inputs of the exclusive OR gate 336; (2) the input of the NOR gate 344 through a 27K resistor 350; and (3) the electrical common through the resistor 350 and a 120 pf capacitor 352.

The output of the exclusive OR gate 342 is electrically connected to one of the two inputs of the exclusive OR gate 340, the other input being electrically connected to a source 138 of a positive 8 volts. The output of the exclusive OR gate 336 is electrically connected to a source 138 of a positive 8 volts. The output of the exclusive OR gate 336 is electrically connected to the up-down counter circuit 332 through a conductor 354 and the output of the OR gate 340 is electrically connected to the up-down counter circuit 332 through a conductor 356 to provide signals corresponding to the first and second sensor thereto modified so that signals received from the first sensor before the second count up and signals received by the second sensor before the first sensor count down.

The up-down counter circuit 332 includes a type 4029 up-down counter 360 and a type 4002B NOR gate 362. Conductor 354 is electrically connected to pin 15 of the counter 360 to cause it to count up and conductor 356 is electrically connected to pin 10 of the counter 360 to cause it to count down and to one of the four inputs of the NOR gate 362, the output of which is electrically connected to pin 5 to inhibit counting upon receiving a signal on conductor 356 passing through the NOR gate 362.

Pins 2, 14 and 11 of the counter 360 are each electrically connected to: (1) a different one of the other three inputs of the NOR gate 362; and (2) a different one of the 10K resistor 364, 22K resistor 366 and 39K resistor 368. The other end of the resistors 364, 366 and 368 are each electrically connected to: (1) pin 6 of the counter 360 through an 82K resistor 370; and (2) the electrical common through a 1K resistor 372. Pins 8 and 4 of the counter 360 are grounded and pins 16, 13, 12, 9 and 3 are electrically connected to the source 138 of a positive 8 volts to determine the output voltage of the counter. Pins 1 and 7 are electrically connected to conductors 374 and 376 to provide output positive 8 volt pulses as the counter counts in binary notation upwardly in response only to signals caused by rotation of the motor in the direction which enables the piston to force fluid from the cylinder of the pump. The counter counts downwardly in response to reverse rotation but is inhibited from counting past zero.

To divide the binary signals applied on conductors 374 and 376 in two, the divide-by-two circuit 330 includes a type 4013B divider 374 having pins 3 and 11 electrically connected to conductor 376 and pin 13: (1) electrically connected to conductor 374 and to pin 10 through a 2.7K resistor 380; and (2) to the electrical common through resistor 380 and a 0.01 uf capacitor 382. Pins 9 and 14 of the divider 378 are each electrically connected to the source 138 of a positive 8 volts, pin 1 is electrically connected to conductor 290 to provide a frequency output representing the rate of flow of effluent from the pump, pins 2 and 5 are electrically connected together and pins 4, 6, 8 and 7 are each electrically connected to the electrical common.

Figure 13:
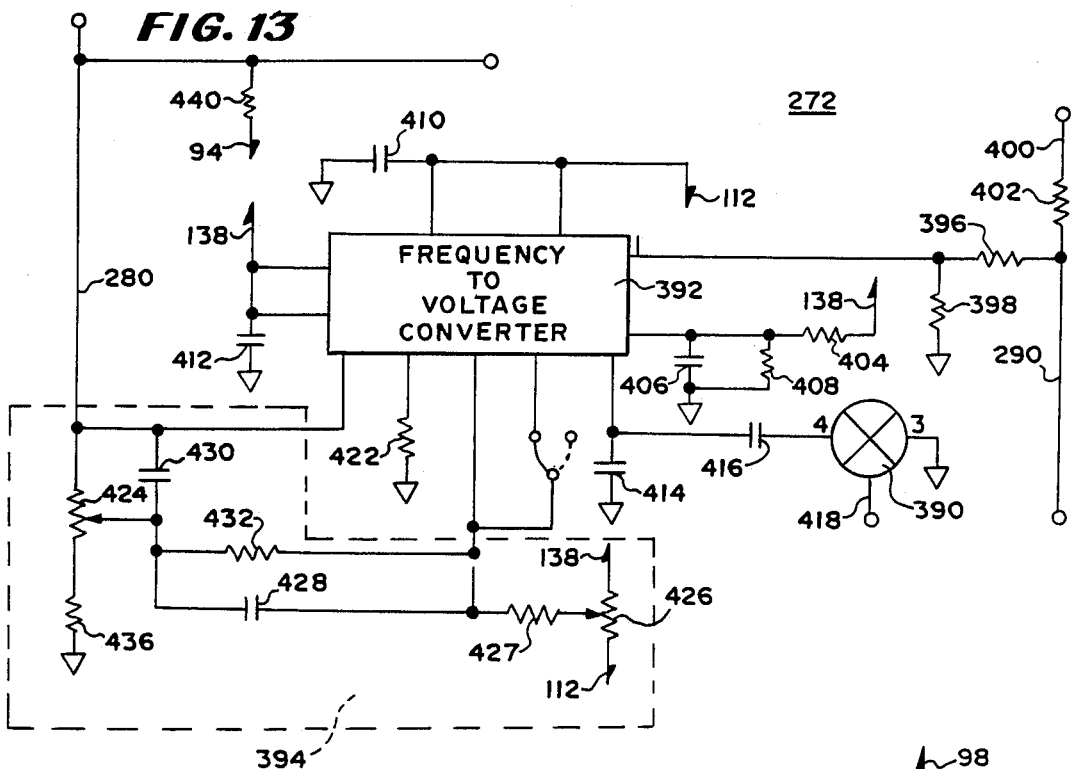
FIG. 13 is a schematic circuit diagram of a portion of the block diagram of FIG. 9.

In FIG. 13, there is shown a schematic circuit diagram of a frequency to voltage converter 272 (FIG. 9) having an analog switch 390, an LM2907 frequency to voltage converter 392 and a gain adjustment circuit 394.

The frequency to voltage converter may be any suitable type, many of which are known in the art but in the preferred embodiment it is an integrated circuit sold by National Semiconductor under the disignation LM2907. Pin 1 of that unit is electrically connected to conductor 290 to receive pulses from the tachometer disc and sensor system 58 (FIG. 3 and 8) through a 22K resistor 396. This circuit is part of a tachometer that produces an output voltage porportional to motor speed.

The conductor 290 is also electrically connected to the electrical common through the resistor 396 and a 22K resistor 398 and to the system controller 22 (FIG. 1) through a 10K resistor 402 and a conductor 400 where it may be used by the system to indicate the progress of the chromatographic run. The frequency to voltage converter 392 has pin 11 electrically connected: (1) through a source 138 of a positive 8 volts and a 47K resistor 404 for biasing; and (2) through a 0.47 uf capacitor 406 and a 15K resistor 408 to the electrical common in parallel to short out noise. Pins 7 and 12 are electrically connected to a source 112 of a negative 8 volts and to the electrical common through a 1 uf capacitor 410, pins 8 and 9 electrically connected to a source 138 of a positive 8 volts and to the electrical common through a 1 uf capacitor 412.

To accommodate changes in pumping speed, the frequency to voltage converter 392 has pin 2 electrically connected to: (1) the electrical common through an 820 pf capacitor 414; and (2) one lead of 4016 analog switch 390 through an 820 pf capacitor 416. The gate of the analog switch 390 is connected to conductor 418 to receive a low range signal and the other level is electrically connected to the electrical common.

The switch 390 doubles the gain of the frequency to voltage converter by doubling capacitance by switching capacitor 416 in parallel with 414 to provide low range operation at a high scale with an additional multiplier to be described hereinafter upon receiving a signal on conductor 418.

To control the gain of the voltage conversion provided by frequency to voltage converter 392, the gain control circuit 394 includes a first 5K potentiometer 424 and a second 5K potentiometer 426 with the potentiometer 426 being connected at one end to a source 138 of a positive 8 volts and at the other end to a source 112 of a negative 8 volts, its variable tap being electrically connected through a 10 megaohm resistor 427 to: (1) pin 10 through a switch which may be opened or closed; (2) and pin 3 of the frequency to voltage converter 392; (3) pin 5 through a 0.022 uf capacitor 428 and a 0.33 uf capacitor 430; and 4 and to the tap of the potentiometer 424 through a 30.9K resistor 432.

The potentiometer 424 is electrically connected at one end to a conductor 280 and to pin 5 of the frequency to voltage converter 392 and at its other end to the electrical common through a 10K resistor 436 and directly to pin 5 of the frequency to voltage converter and to pin 5 of the voltage to frequency converter through the capacitor 430. Conductor 280 applies the voltage corresponding to the rate of flow of fluid to the exponential amplifier circuit 276 (FIG. 9) through conductor 280 and to the first compensation circuit 40 (FIG. 2). Conductor 280 is electrically connected to the source 94 of a negative 12 volts through a 604 ohm resistor 440.

With this arrangement, the amplitude of the voltage output may be adjusted by potentiometer 424 and 426 to provide a voltage which varies in relation to the rate of flow of fluid as measured by the tachometer. This voltage is applied to the first compensation circuit 40 (FIG. 2) for application to the linear flow rate control circuit 38 (FIG. 2) and to the exponential amplifier circuit 276 (FIG. 9) through conductor 280 to control the nonlinear flow control circuit 42 (FIG. 2).

Figure 14:
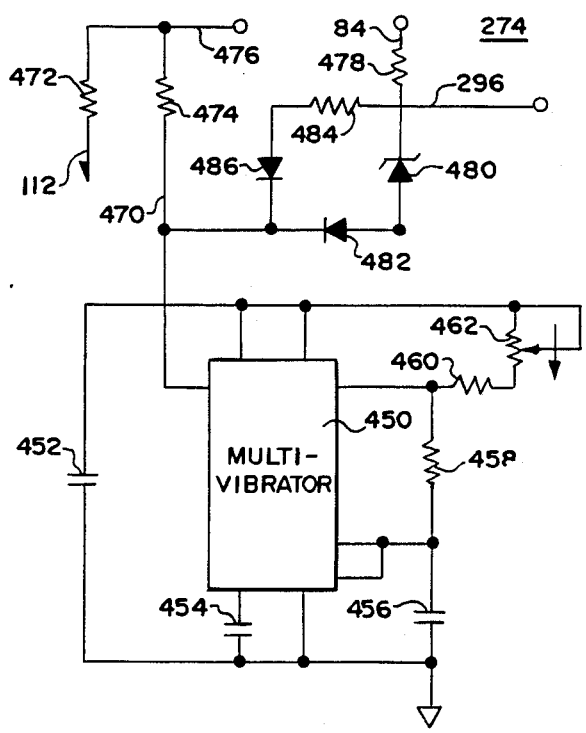
FIG. 14 is a schematic circuit diagram of still another portion of the block diagram of FIG. 9.

In FIG. 14, there is shown a schematic circuit diagram of the multivibrator circuit 274 (FIG. 9) having a conventional astable multibrator 450 which may be of any conventional designation but in the preferred embodiment is a National Semiconductor 55 multivibrator connected as shown to provide a suitable frequency during a portion of the time normally required for a full piston stroke of the pump. The function of the multivibrator circuit is to reset the overload circuit and the ramp generator.

To provide the proper frequency, the miltivibrator circuit 274 includes: (1) 3 capacitors 452, 454 and 456 having values of 1 uf, 0.01 uf and 2200 pf respectively; (2) 2 resistors 458 and 460 having values of 680 ohms and 39.2 ohms respectively; and (3) a 10K potentiometer 462 with pins 4 and 6 of the multivibrator 450 being electrically connected to one end of the potentiometer 462, pin 7 being electrically connected to: (1) to the other end of the potentiometer 462 through the resistor 460; (2) pins 6 and 2 of the multivibrator 450 through the resistor 458; and (3) to the electrical common through the capacitor 456. The electrical common is also electrically connected to pin 1, to pin 5 through the capacitor 454 and to pins 4 and 8 through the capacitor 452.

To reset the ramp generator 278 (FIGS. 9 and 16) and to the flow rate control circuit 32 (FIGS. 2, 3 and 4) the output, of the multivibrator 450 is electrically connected to conductor 470 to apply a positive pulse thereto. To provide a signal to the ramp circuit to initiate a ramp, the multivibrator 274 includes a source 112 of a negative 8 volts electrically connected to conductor 470 through a 3.9K resistor 472 and a 1.82K resistor 474 with output conductor 476 being electrically connected to resistor 472 and 474 to change from a negative to a positive value upon receiving a signal from the multivibrator 450. conductor 476 is electrically connected to the ramp generator 278 (FIGS. 9 and 16) to reset it as described hereinafter in connection with FIG. 16. (FIG. 9).

To provide a turn-off signal on conductor 84 to the flow rate circuit 32 (FIGS. 2, 3 and 4) conductor 84 (FIGS. 4 and 14) is electrically connected to conductor 470 through a 680 ohm resistor 478, the reverse resistance of CR106 zener diode 480 and the forward resistance of a 1N914 diode 482.

To reset the overcurrent sensor 60, (FIGS. 3 and 7) conductor 296 to the overcurrent sensor 60 is electrically connected through a 680 ohm resistor 484 and through the forward resistance of a 1N914 diode 486 to conductor 470 to apply a positive potential thereto, permitting the flow rate circuit 32 (FIGS. 2, 3 and 4) to operate.

Figure 15:
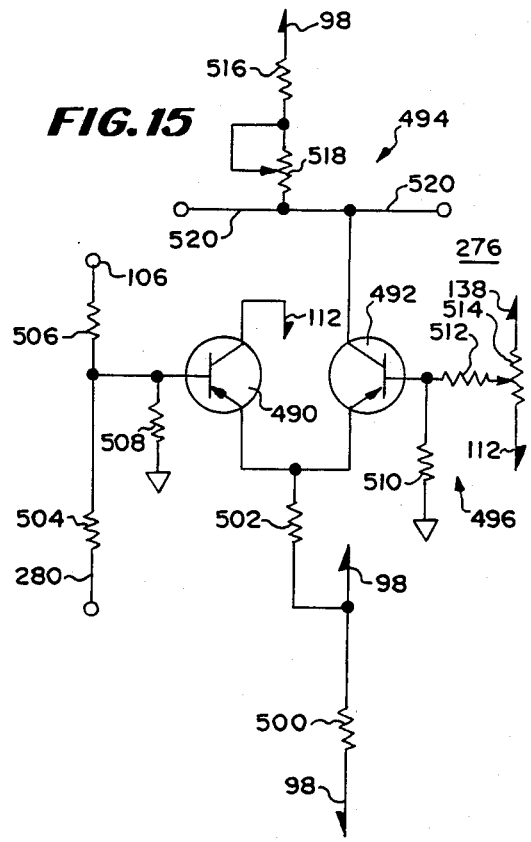
FIG. 15 is a schematic circuit diagram of still another portion of the block diagram of FIG. 9.

In FIG. 15, there is shown a schematic circuit diagram of the exponential amplifier circuit 276 (FIG. 9) having a first PNP 2N3702 transistor 490, a second PNP 2N4061 transistor 492, an adjustment circuit 496 and a bias circuit 494. The transistor 490 has a lower input impedance than transistor 492 and conducts approximately ten times the current through transistor 492. Thus, transistor 492 follows the potential on conductor 280, and provides an exponential drop between the emitter and base of transistor 492. The two transistors cancel their temperature coefficients. The first transistor 490 receives an input signal from the frequency to voltage converter 272 (FIGS. 9 and 13) on conductor 280 indicating the speed of pumping and varies the emitter bias of the transistor 492 to cause an exponential amplification of the signal from the frequency to voltage converter 272 for application through a conductor to the ramp generator circuit 278 (FIG. 9).

To provide emitter biasing to the first and second transistors 490 and 492, the emitters of each of these transistors is electrically connected to a source 98 of a positive 12 volts through a 1.18K resistor 502 and to a second such source through the 1.18K resistor 502 and a 33 ohm resistor 500.

To vary the emitter potential of the second transistor 490 in a manner related to the input amplitude on conductor 280 from the frequency to voltage converter 272 (FIGS. 9 and 13) so as to provide an exponential transfer function, the base of the transistor 490 is electrically connected to: (1) the electrical common through a 47.5 ohm resistor 508; (2) to input conductor 280 through a 1.40K resistor 504; and (3) to a source 106 of a positive 32 volts through a 45.3K resistor 506. The collector of the transistor 490 is electrically connected to a source 112 of a negative 8 volts so that it will draw current through the emitter biasing circuit from the source 98 of a positive 12 volts and through the resistor 502 in proportion to the input signal on conductor 280 and thus cause a drop in the positive potential on the emitter of the transistor 492 as the current increases.

To provide a further adjustment on a sawtooth waveform to be controlled by the transistors 490 and 492, the adjustment circuit 496 includes a 1.18K resistor resistor 510, a 100K resistor 512 and a 5K potentiometer 514. To establish biasing, one end of the potentiometer 514 is electrically connected to a source 138 of a positive 8 volts and the other end is electrically connected to a source 112 of a negative 8 volts, with the movable tap being electrically connected to the base of the transistor 492 through a 100K resistor 512. The base of the transistor 492 is also electrically connected to the electrical common through a 1.18K resistor 510 to provide biasing. The collector of the transistor 492 is connected to conductor 520 to provide an exponentially decreasing amplification of the signal received on conductor 280.

To provide a continuous bias on conductor 520, the bias circuit 494 includes a 150K resistor 516 and a 500K potentiometer 518. The resistor 516 and potentiometer 518 are electrically connected between a source 98 of a positive 12 volts and the conductor 520 to permit adjustment of the voltage drop for application of a current to the ramp generator 278.

Figure 16:
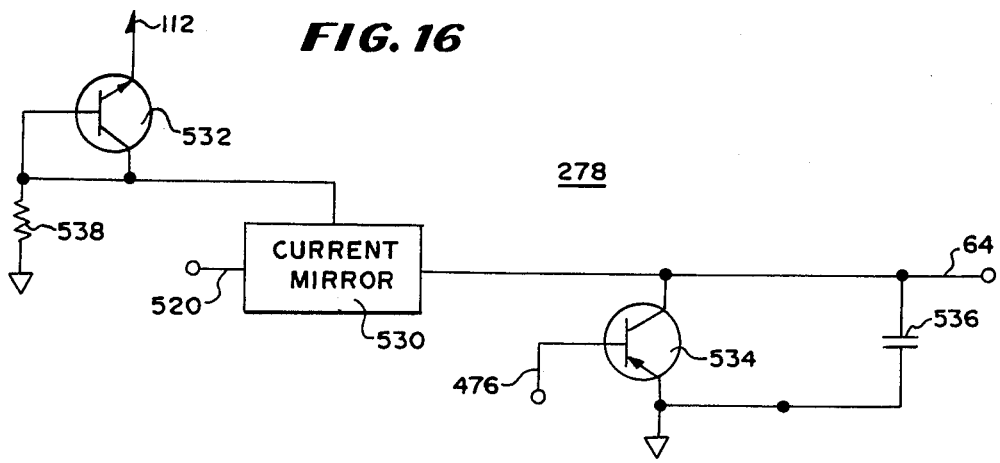
FIG. 16 is a schematic circuit diagram of still another portion of the block diagram of FIG. 9.

In FIG. 16, there is shown a schematic circuit diagram of the ramp generator 278 (FIG. 9). To form a ramp which varies in slope in a manner related to the output from the exponential amplifier 276 (FIGS. 9 and 15) for application to the flow rate circuit 32 (FIGS. 2 and 4) the ramp generator circuit 278 includes a type TL011C current mirror 530 made and sold by Texas Instruments, a 2N3710 NPN transistor 532, a 2N4403 PNP transistor 534, and a 910 pf capacitor 536. The current mirror 530 has its input electrically connected to conductor 520 to receive the output of the exponential amplifier circuit 276 (FIGS. 9 and 15) and its output electrically connected to conductor 64 to apply current which decreases as the motor speed increases from a high output impedance source with a gain of 1 to draw current from capacitor 536 across to generate a negative going ramp from the capacitor.

The common of the current mirror 530 is electrically connected to the collector of diode connector transistor 532 through which it conducts current. The emitter of the transister 532 is electrically connected to a source 112 of a negative 8 volts to control the bias on current mirror 530. The 2.7K resistor 538 keeps the voltage at its collector of the transistor 532 relatively constant at about 7.3 volts regardless of the operation of the current mirror 530.

To form a ramp from the output of the current mirror 530, conductor 64 is electrically connected to its output and to one plate of the capacitor 536, the other plate of which is electrically connected to the emitter of transistor 534. With this arrangement, the current flowing from the output of the current mirror 530 charges capacitor 536 to form a ramp potential on conductor 64.

To reset capacitor 536, the transistor 534 has its collector electrically connected to conductor 64 and its base electrically connected to the multivibrator circuit 274 (FIGS. 9 and 14) through conductor 476 so that when the multivibrator provides a negative pulse at the end of a ramp, transistor 534 becomes conducting to discharge capacitor 536. When transistor 534 becomes nonconducting at the end of the negative pulse at its input, the capacitor 536 receives a high impedance between one plate in conductor 64 and low impedance on the other to be in condition to charge and form a ramp potential on conductor 64 as current flows through the current mirror 530.

The current mirror 530 may be any conventional circuit which results in a complementary current flow from its input. In the preferred embodiment, this is a commercial integrated circuit designated TL011c and sold by Texas Instrument.

Figure 17:
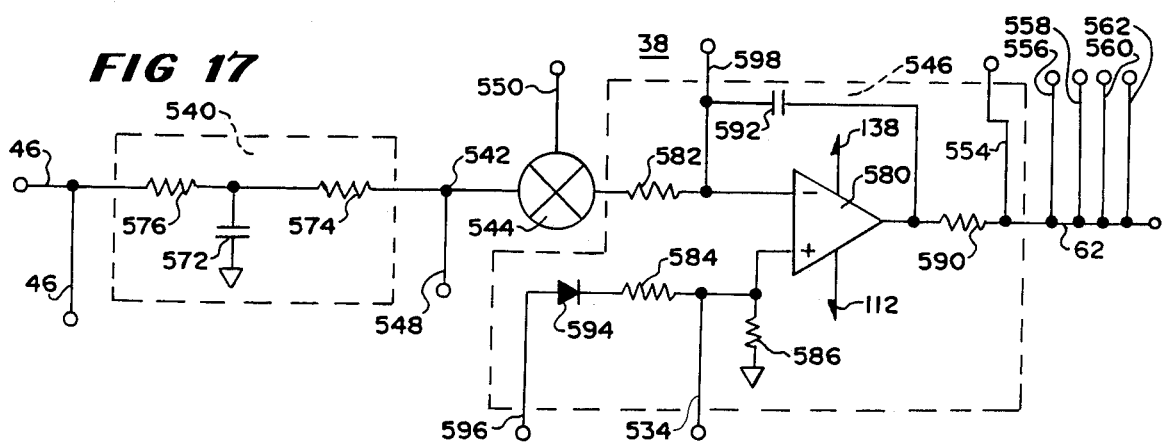
FIG. 17 is a schematic circuit diagram of another portion of the embodiment of the motor control circuit of FIG. 2.

In FIG. 17, there is shown a schematic circuit diagram of the linear flow rate control circuit 38 (FIG. 2) having a reference voltage to current converter 540, a summing node 542, a switch 544, and a servoamplifier circuit 546. The reference voltage to current converter circuit 540 receives a signal indicating the desired constant flow rate of the influent to the chromatographic column on conductor 46 and converts it to a current for application to the summing node 542 where it is summed with a feedback signal. Upon being gated by the gate 544, this signal is applied to the main servoamplifier circuit 546 where it is subtracted from certain other correction signals for application through conductor 62 to the flow rate circuit 32 (FIGS. 2, 3 and 4).

To provide a feedback signal during the delivery portion of a pumping stroke, the summing node 542 receives: (1) a current set to represent the desired flow rate from resistor and low pass filter 540; and (2) a current from conductor 548 (FIG. 19) fed back from the motor circuit 30 (FIG. 2) representing the effluent as corrected by the first compensation circuit 40 (FIG. 2) in a manner to be described hereinafter.

This current is gated by the analog gate 544 under the control of a signal on conductor 550 to the inverting terminal of the servoamplifier 546 where it is summed with a signal from the first compensation circuit 40 (FIG. 2) through a conductor 598.

The main servoamplifier 546 receives a signal from the second compensation circuit 44 (FIG. 2) through a conductor 554 and the difference between the two signals is applied to conductor 62. Conductor 62 at different times receives compensation circuits on conductors 556 to provide servo gain and certain compensations such as for compressibility of the fluids, logic signals on conductor 558, a refill gain correction signal on conductor 560, and a gain from the braking circuit on conductor 562.

To process the set point voltage on conductor 46 and apply to summing node 542, the reference voltage to current converter 540 includes a 10K resistor 570, a 0.1 uf capacitor 572, and a 187K resistor 574. The resistor 570 is electrically connected at one end to conductor 46 and at its other end to the electrical common through the capacitor 572 and the summing node 542 through the resistor 574.

The switch 544 is a type 4016 integrated circuit switch sold by the aforementioned National Semiconductor although any suitable electronically operated switch may be used. The switch 544 is electrically connected to be controlled by the first compensation circuit 40 (FIG. 2).

To compare the signal on conductor 548 fed back from the motor tachometer, with the signal on conductor 46 indicating the desirable flow rate, the servoamplifier circuit 546 includes an LM 353 differential amplifier 580 sold by National Semiconductor, four resistors 582, 584, 586 ad 590, a 22 pf capacitor 592, and a 1N914 diode 594. The resistors are a 470 ohm resistor 582, a 10K resistor 584, a 47K resistor 586 and a 220 ohm resistor 590. The resistor 582 is electrically connected at one end to the output of the switch 544 and at its other end to: (1) the inverting input terminal of the amplifier 580 to supply a signal thereto representing the flow rate error signal; and (2) conductor 598 electrically connected to the first compensation circuit 40 (FIG. 2); and (3) to the output of the differential amplifier 580 through the capacitor 592.

The output of the amplifier 580 is electrically connected to conductor 62 through the resistor 590 and the amplifier has a source 138 of a positive 8 volts connected as one rail at pin 8 and a source 112 of a negative 8 volts connected as a second rail at pin 4. The noninverting input terminal of the amplifier is electrically connected to: (1) the electrical common through the resistor 586; (2) conductor 554 to receive the feedback pumping rate signal; and (3) a conductor 596 through the forward resistance of the diode 594 and the resistor 584 for placing the pump in the stop mode. Conductor 596 receives a signal from a start circuit under the control of the system controller 22 (FIG. 1).

Figure 18:
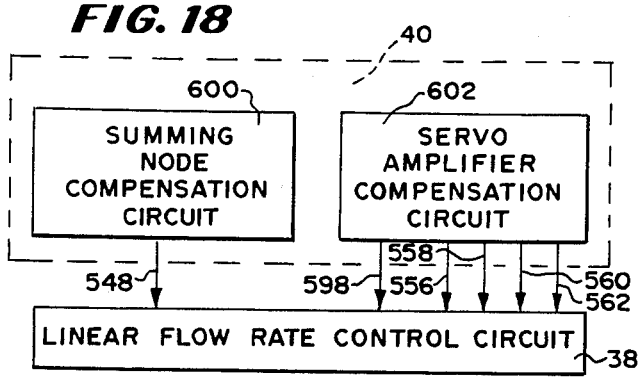
FIG. 18 is a block diagram of still another portion of the block diagram of FIG. 2.

In FIG. 18, there is shown a block diagram of the first compensation circuit 40 (FIG. 2) as it is electrically connected to the linear flow rate control circuit 38 (FIGS. 2 and 17). The first compensation circuit 40 includes a summing node compensation circuit 600 and a servoamplifier compensation circuit 602 each electrically connected to the linear flow rate control circuit 38 at different locations, with the summing node compensation circuit 600 being electrically connected to the summing node 542 (FIG. 17) and the servoamplifier compensation circuit 602 being electrically connected to the servoamplifier inverting input at 598 and at its output as shown at 556, 558, 560 and 562 (FIG. 17).

With this arrangement, the speed of the motor is corrected by the range of fluid that is flowing, the measured average flow of the influent into the chromatographic column and for certain factors such as the braking gain, refill gain, servo gain and liquid compensation or for braking values at the input to the servoamplifier.

Figure 19:
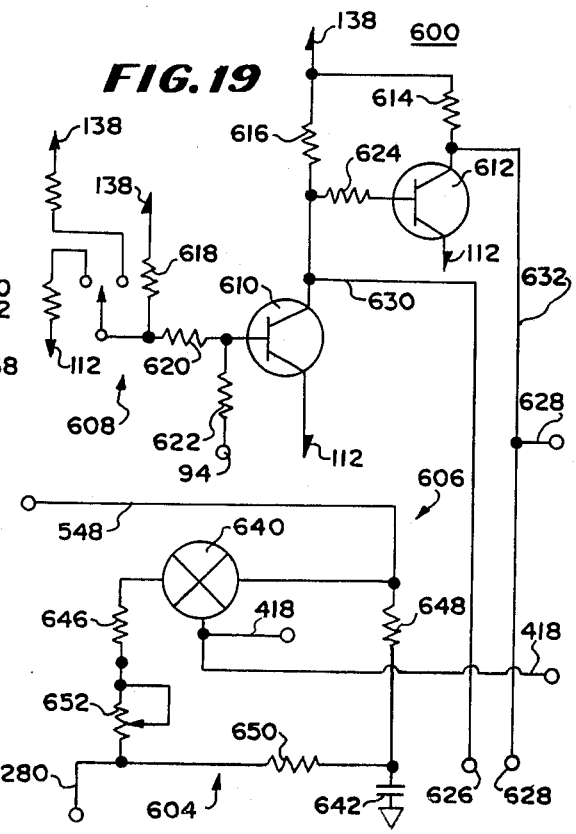
FIG. 19 is a block diagram of another portion of the block diagram of FIG. 2.

In FIG. 19, there is shown a schematic circuit diagram of the summing node compensation circuit 600 (FIG. 18) having a range selection circuit 608 and coupling circuit shown generally at 604. The range selection circuit 608 may energize either a high or low voltage levels current to be applied to the coupling circuit 604 which receives the variable amplitude voltage from the frequency to voltage converter 272 (FIGS. 9 and 13) on conductor 280 and converts it to a current applied through conductor 548 to the summing node. The magnitude of the current depends on whether a high or low range is selected. While a range selection circuit 608 is shown connected to conductor 630, in the preferred embodiment, a signal from the microprocessor is used to energize the transister 610 and open switch 640. In this specification, a high signal is applied to terminals 628 to select a one-tenth scale set point and corresponding feedback signals and terminals 626 or 418 from a low range in which the signals are subject to less attenuation by a factor of 10.

To provide a larger or smaller current depending on the selection of a high or low range, the range selection circuit 608 includes a 2N3704 NPN transistor 610, a 2N3704 NPN transistor 612 and seven resistors which are respectively a 2.2K resistor 614, a 2.2K resistor 616, a 230 ohm resistor 618, a 2.43K resistor 620, 1K resistor 622, and a 22K resistor 624.

To provide a low range current, the transistor 610 has its emitter electrically connected to a source 112 of a negative 8 volts, its base electrically connected to: (1) a source 94 of a negative 12 volts through the resistor 622; and (3) a source 138 of a positive 8 volts through resistors 618 and 620 in series and has its collector electrically connected to: (1) a contact 626 within the range selection circuit 608 for a low range current; (2) the base of transistor 612 through resistor 624; and (3) a source 138 of a positive 8 volts through the resistor 616.

The emitter of the transistor 612 is electrically connected to a source 112 of a negative 8 volts and its collector is electrically connected to a source 138 of a positive 8 volts through the resistor 614. The range selection circuit 608 has a movable contact which connects a source of positive potential to either the low range switch 626 or the high range switch 628, the low range switch placing a voltage on conductor 630 and the high range switch placing a voltage on conductor 632.

The conductor 630 is electrically connected through conductor 418 to the frequency to voltage converter 272 (FIGS. 9 and 13) to ground the capacitor 410 (FIG. 13), thus increasing the amplitude of the output potential.

To convert potential to current for application to the summing node 542 (FIG. 17) through conductor 548, the coupling circuit 604 includes an analog switch 640, a 0.047 uf capacitor 642, three resistors and a 5K potentiometer 652. The three resistors are an 11.5K resistor 646, a 49.9K resistor 648 and a 4.7K resistor 650. Conductor 280 from the output of the voltage to frequency converter 272 (FIGS. 9 and 13) is electrically connected to: (1) the input of the switch 640 through the potentiometer 652 and the resistor 648; and (2) electrical common through the resistor 650 and the capacitor 642. The gate of switch 640 is electrically connected to conductors 630 and 418 and its output is electrically connected to electrical common through the resistor 448 and the capacitor 642.

Figure 20:
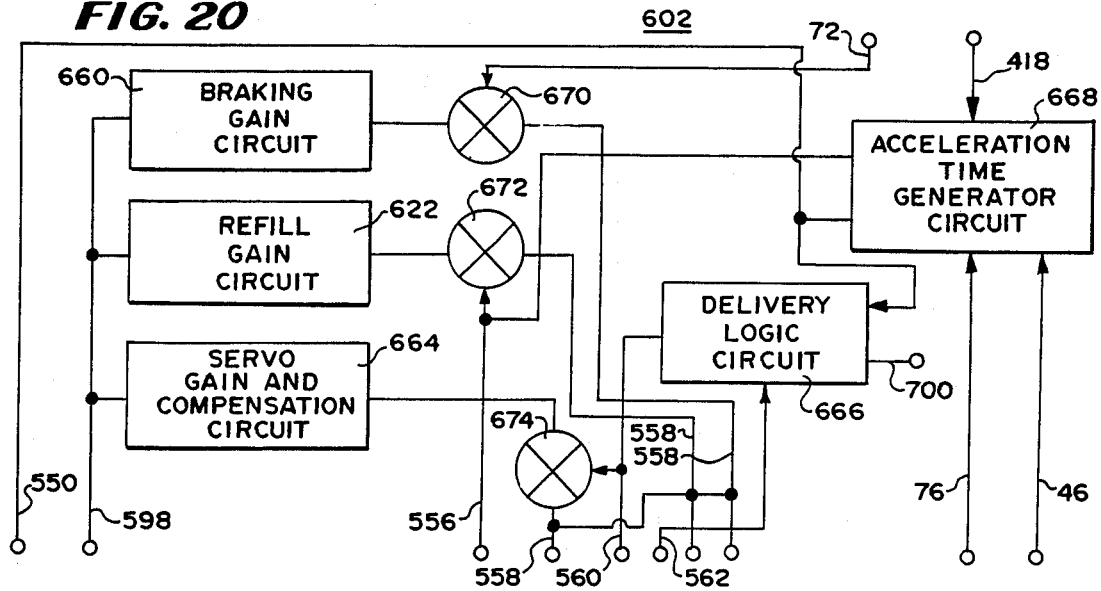
FIG. 20 is a block diagram of a portion of the block diagram of FIG. 18.

In FIG. 20, there is shown a block diagram of the servoamplifier compensation circuit 602 (FIG. 18), having a braking gain circuit 660, a refill gain circuit 662, a servo gain and compensation circuit 664, a delivery logic circuit 666, and an acceleration time generator circuit 668. Each of these circuits generates signals relating to the timing of the acceleration of the pump motor and applies the signal to the linear flow rate control circuit 38 (FIGS. 2 and 17) through a plurality of analog switches. The analog switches are 670, 672 and 674.

For this purpose, the acceleration time generator circuit 668 applies signals to the delivery logic circuit 666 and to conductor 550 through one conductor and to the switch 672 through another conductor. The switch 670 is controlled by a signal on conductor 72 from the brake circuit 52 (FIGS. 3 and 5) to apply a brake gain through conductor 560 and a servo gain from the servo gain and compensation circuit 664 through conductor 558 by opening switch 674. The refill gain is applied from the refill gain circuit 662 upon being opened by a signal from the acceleration time generator circuit 668 indicating a refill cycle.

Figure 21:
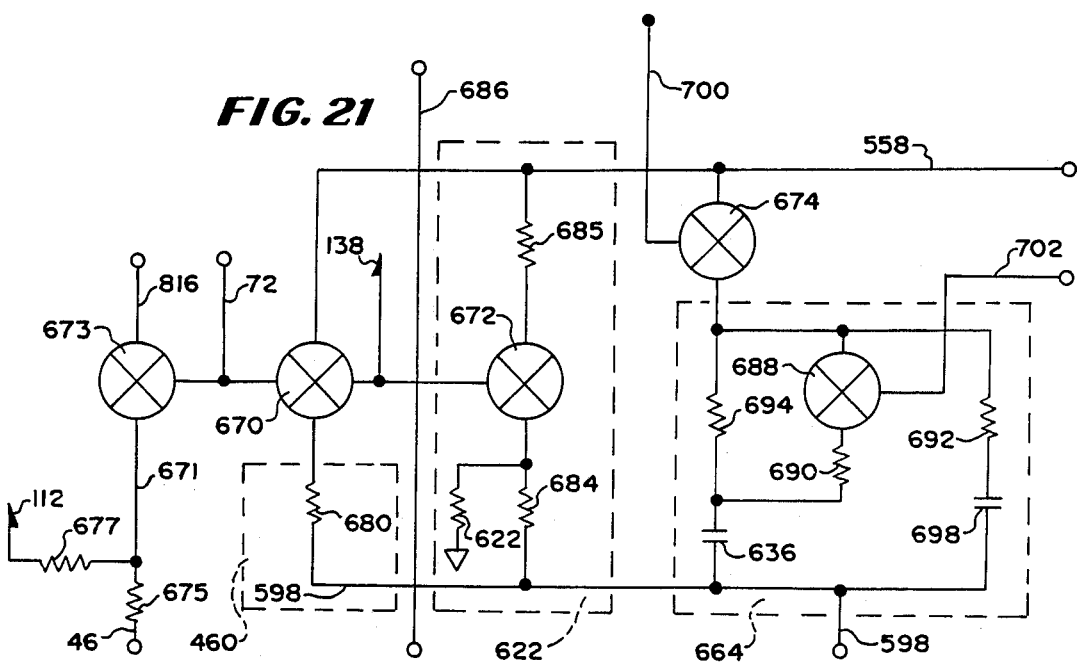
FIG. 21 is a block diagram of another portion of the block diagram of FIG. 18.

In FIG. 21, there is shown a schematic circuit diagram of the braking gain circuit 660, the refill gain circuit 662, and the servo gain and compensation circuit 664 and their associated switches 670, 672 and 674 (FIG. 20). The braking gain circuit 660 is controlled by switch 670, the refill gain circuit 662 is controlled by switch 672 and the servo gain and compensation circuit 664 is controlled by the switch 674 to which they are connected to apply currents through conductor 598 to the flow rate control circuit 38 (FIGS. 2 and 17) to change the speed of the motor in accordance with corrections required for braking, refill and servo gain and compensation.

The braking gain circuit 660 includes a 4.7M resistor 680 electrically connected at one end to the output switch 670 and at its other end to conductor 598 to attenuate the signal on conductor 598 during a braking cycle. Switch 670 has its gate input electrically connected to conductor 72 from the brake circuit 52 (FIG. 3) and its input electrically connected to the conductor 558. The analog switch controls the gain and applies an attenuated voltage of the servo amplifier. The level of the set point signal on conductor 46 is level shifted by the 7.5K resistor 677, the negative source 112 and the 2.05K resistor 675 to be applied to conductor 816 when switch 673 is opened.

The refill gain circuit 662 includes a 68K resistor 682 and a 1.2M (megohm) resistor 684. The resistor 682 is electrically connected to the electrical common at one end and connected to the one lead of the switch 672 and the resistor 682 is electrically connected at one end to conductor 598 to apply a signal to the linear flow rate control circuit 38. Switch 672 has its gate electrically connected to conductor 560 to the delivery logic circuit 666 (FIG. 20) and the second drain electrically connected through conductor 686 to the second compensation circuit 44 (FIG. 2).

To control servo gain and thus to provide servo stability, the servo gain and compensation circuit 664 includes an analog switch 688, two 3.3M resistors 690 and 692, a 180K resistor 694, a 0.22 uf capacitor 696 and a 0.047 uf capacitor 698. One lead of the switch 688 is electrically connected through the resistor 690 and the capacitor 696 in series to conductor 598 to apply a compensation signal thereto. The other lead of the switch 688 is electrically connected to: (1) the capacitor 696 through resistor 694; (2) one lead of the switch 694; (3) conductor 598 through the resistor 692 and the capacitor 698 in series.

To control the servo gain and compensation circuit, the switch 674 has its gate electrically connected to the delivery logic circuit 666 (FIG. 20) through conductor 700 (FIG. 20). With this arrangement, signals from the delivery logic circuit 666 are applied to the gate of switch 674 to close this switch and carry signals from resistors 692 and 694 and switch 688 providing the required compensations.

The refill gain circuit 662 (FIG. 20) upon receiving a signal on conductor 566 from the acceleration time generator circuit 668 indicating a refill cycle provides a feedback path for the servo amplifier through a resistive network including resistors 682, 684 and 685 to conductor 598 and the servo gain and compensation circuit 664 closes an additional feedback path for the servo amplifier through a resistance network including a signal applied to switch 688 on conductor 702.

Figure 22:
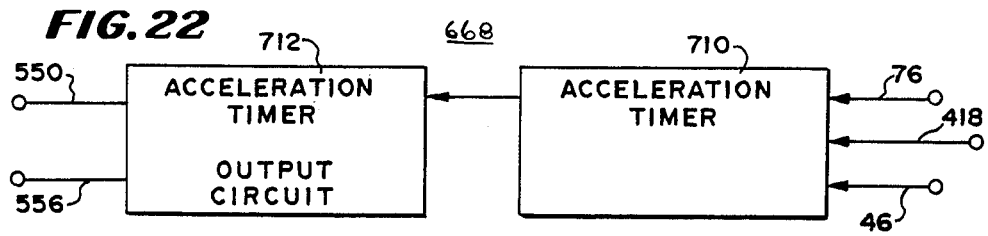
FIG. 22 is a schematic circuit diagram of a portion of the block diagram of FIG. 20.

In FIG. 22, there is shown a block diagram of the acceleration timer generator circuit 668 (FIG. 20) having an acceleration timer 710 and an acceleration timer output circuit 712. The acceleration timer 710 is electrically connected to conductor 76 to receive a refill inception signal, conductor 418 to receive a signal indicating the compressibility of the fluid being pumped and a signal on conductor 46 indicating the set flow rate.

The acceleration timer 710 processes these signals and applies a signal to the acceleration timer output circuit 712 and two conductors 550 and and 556 to speed up the motor at the end of fluid delivery at an accelerating rate to make up for fluid flow that will be lost during a time period before delivery commences again.

The acceleration timer 710 receives a signal indicating the start of the refill cycle and causes a time limit on motor acceleration while there is no flow so that the cylinder is filled across the period of time controlled by the timer. The motor may also be caused to accelerate in a forward stroke in a manner controlled by the acceleration timer 710 if the forward stroke starts during this time period. The time is increased as the flow rate increases.

Figure 23:
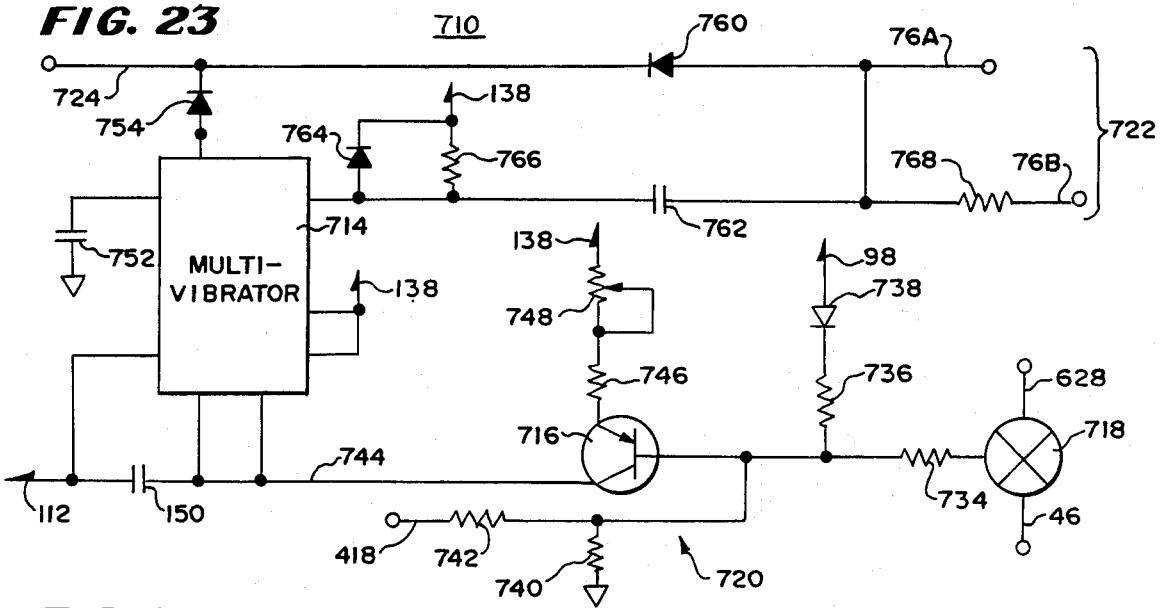
FIG. 23 is a schematic circuit diagram of a portion of the block diagram of FIG. 22.

In FIG. 23, there is shown a schematic circuit diagram of the acceleration timer 710 having a monostable multivibrator 714, a 2N4403 PNP transistor 716 and an analog switch 718. The multivibrator 714 is type 555 sold by National Semiconductor Corporation identified above but any monostable multivibrator may be used provided it is designed to have satisfactory parameters in a manner known in the art.

To provide an output signal to conductor 724 related to the motor acceleration, the acceleration timer 710 has a time duration circuit 720, a connection to lead 418 which carries a signal indicating the compressiblity of the fluid being pumped and an output conductor 724, all of which are electrically connected to the multivibrator 714 so that the amplitude adjustment circuit 720 provides correction amplitude for high or low range, calibration and compression of liquids.

To trigger the monostable multivibrator 714, conductor 76A from the output of the comparator 184 (FIG. 6) drives conductor 724 high at inception of the refill stroke and goes low at the end of the signal and a short time later. It is differentiated by capacitor 762 to trigger the multivibrator to high and maintaining lead 724 high until the timer drops low under the control of capacitor 150 and current through transistor 716 to remove potential from conductor 724.

To permit adjustment of the signal on conductor 744 electrically connected to the collector of the transistor 716, the emitter of the transistor is electrically connected to a source 138 of a positive 8 volts through a 16.5K resistor 746 and a 10K potentiometer 748. The transistor 716 is a type 2N4403 and the adjustment of the potentiometer 748 adjusts the current applied to conductor 744 through its collector so as to permit adjustment of the acceleration time of the motor.

Conductor 744 is electrically connected to pins 6 and 7 and to the source 112 of a negative 8 volts through a 1 uf timing ramp capacitor 150, the source 112 being electrically connected to pin 1 and pins 4 and 8 being electrically connected to the source 138 of a positive 8 volts, whereby the time duration of the output pulse width from the multivibrator 714 is adjusted. Pin 5 of the multivibrator 714 is electrically connected to electrical common through a 0.01 uf capacitor 752 and pin 3 is electrically connected to conductor 724 through the forward resistance of a diode 1N914 754 to apply the output to conductor 724. The multivibrator 714 is triggered on by the tailing edge of a signal applied through conductors 76A and 76B from the refill initiator.

To trigger the multivibrator 714, the trigger circuit 722 includes a 1N914 diode 760, a 0.22 uf capacitor 762, a 1N273 diode 764, a 47K resistor 766 and a 3.74K resistor 768. Conductor 76B is electrically connected to conductor 76 through the resistor 768. Conductor 76B is electrically connected to conductor 76 through the resistor 768 and to pin 2 of the multivibrator 714 through the capacitor 762. Pin 2 is also electrically connected to the source 138 of a positive 8 volts through the resistor 766 and the forward resistance of the diode 764. Conductor 76A is electrically connected to conductor 724 through the forward resistance of diode 760 and to the cathode of the diode 754 so that, a pulse differentiated by capacitor 762 and resistor 47K triggers the multivibrator 714 to apply a potential to conductor 724.

Figure 24:
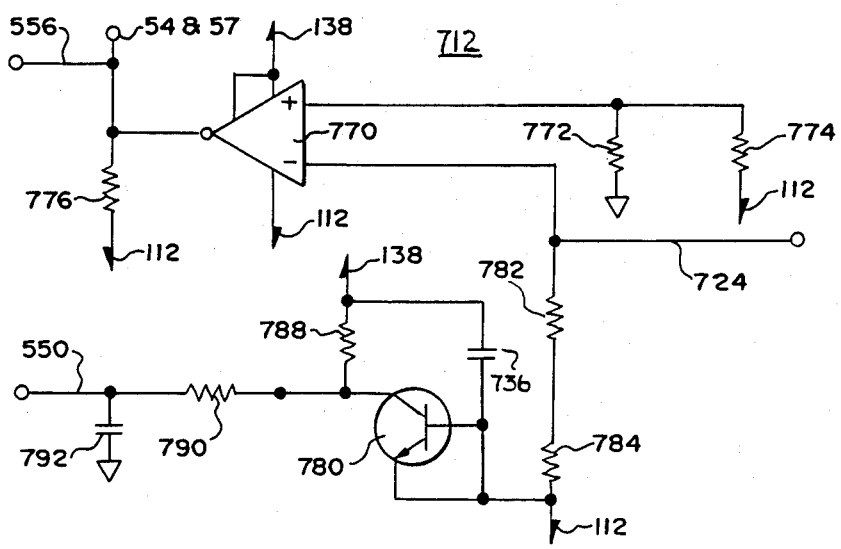
FIG. 24 is a schematic circuit diagram of another portion of the block diagram of FIG. 22.

In FIG. 24, there is shown a schematic circuit diagram of the acceleration timer output circuit 712 (FIG. 22) which receives a signal on conductor 724 to establish acceleration across a predetermined period of time and supplies signals to conductors 686 to close switch 672 (FIG. 21) and apply compensation from the refill gain circuit 662 (FIGS. 20 and 21) and conductor 550 to open switch 544 (FIG. 17) to disconnect potential from the summing node 542 (FIG. 17) to the servoamplifier 580 (FIG. 17).

To generate a signal for conductor 556, the output circuit includes a first LM 311 comparator 770 having its inverting input terminal electrically connected to conductor 724 and its noninverting input terminal electrically connected to: (1) electrical common through a 2.43K resistor 772; and 2 to a source 112 of a negative 8 volts through a 4.7K resistor 774. The comparator 770 has one rail electrically connected to a source 138 of a positive 8 volts and the other rail electrically connected to a source 112 of a negative 8 volts. Its inverted output terminal is electrically connected to conductor 556 and to a source 112 of a negative 8 volts through a 10K resistor 776.

To apply a signal to switch 544 (FIG. 17), the acceleration timer output circuit 712 (FIG. 22) includes a 2N3704 NPN transistor 780 having its base electrically connected to: (1) conductor 724 through a 15K resistor 782; and (2) to a source 112 of a negative 8 volts through a 2.2K resistor 784. The emitter of the transistor 780 is electrically connected to the source 112 of a negative 8 volts and to a source 138 of a positive 8 volts through a 1 uf capacitor 786. The source 138 of a positive 8 volts is electrically connected to the collector of the transistor 780 through a 4.7K resistor 788 and the collector of the transistor 780 is electrically connected to conductor 550 through a 22K resistor 790. Conductor 550 is connected to electrical common through a 0.1 uf capacitor 792.

Figure 25:
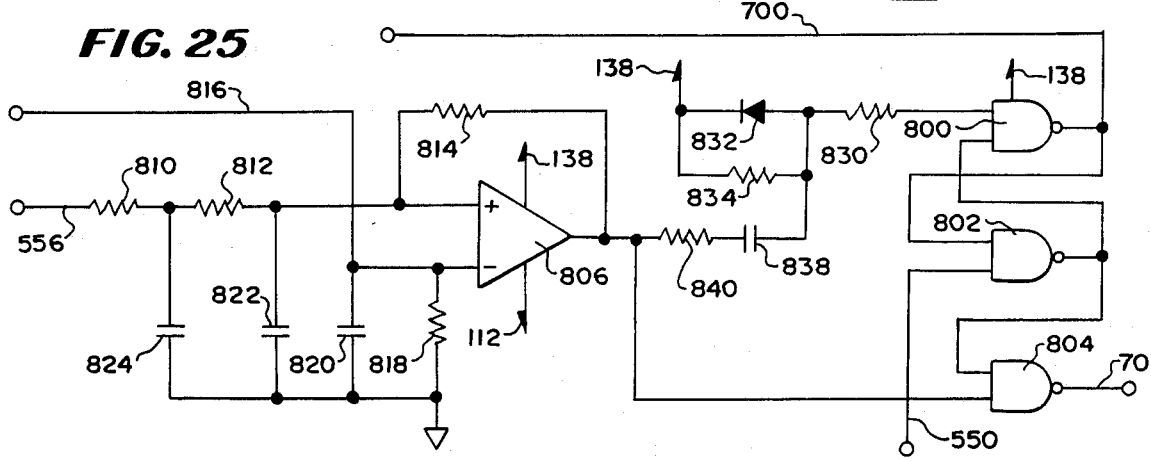
FIG. 25 is a schematic circuit diagram of still another portion of the block diagram of FIG. 20.

In FIG. 25, there is shown a schematic circuit diagram of the delivery logic circuit 666 (FIG. 20) having three NAND gates 800, 802 and 804, respectively, and a differential amplifier 806. The differential amplifier 806 has its noninverting input terminal electrically connected to conductor 556 to receive the output from the main servoamplifier 546 (FIG. 17) through a 10K resistor 810 and a 68K resistor 812 in series. The inverting input terminal of the differential amplifier 806 is electrically connected to: (1) conductor 816 to receive a level shifted set point signal during braking; and (2) the electrical common through a 47K resistor 818 and through a 0.1 uf capacitor 820 in parallel to slow the motor when it is near its constant speed point.

The noninverting input terminal of the differential amplifier 806 is electrically connected to the electrical common through a 220 pf capacitor 822 and through the resistor 812 and a 0.1 uf capacitor 824. With this arrangement, the differential amplifier 806 transmits a negative going signal to one input of the two-input NAND gate 804 during braking. The other input of the NAND gate 804 and conductor 700 are electrically connected to the output of a flip-flop comprising NAND gate 802, one input of the NAND gate 802 being electrically connected to conductor 550 and its other input electrically connected to the output of NAND gate 800.

Conductor 550 goes to a low potential at the start of refill, setting the flip-flop composed of NAND gates 800 and 802. The output of NAND gate 802 is electrically connected to one input of the NAND gate 800 and the other input is electrically connected to: (1) a source 138 of a positive 8 volts through a 4.7K resistor 830 and the forward resistance of a 1N914 diode 832; (2) the source 138 of a positive 8 volts through the resistor 830 and a 220K resistor 834; and (3) the output of differential amplifier 806 through the resistor 830, a 0.001 uf capacitor 838 and a 10K resistor 840 in series in the order names. At the end of the braking period, the servo amplifier output voltage on lead 556 drops below the level shifted setpoint voltage on lead 816. This produces a negative transition at the output of differential amplifier 806 which resets flip-flop 800 and 802 through resistor 840, capacitor 838 and resistor 830. The output of the differential amplifier 806 is electrically connected to one of the two inputs of the NAND gate 804 so as to provide a low output signal for braking only when the flop-flop including NAND gates 800 and 802 is set and the output of differential amplifier 806 is high.

Figure 26:
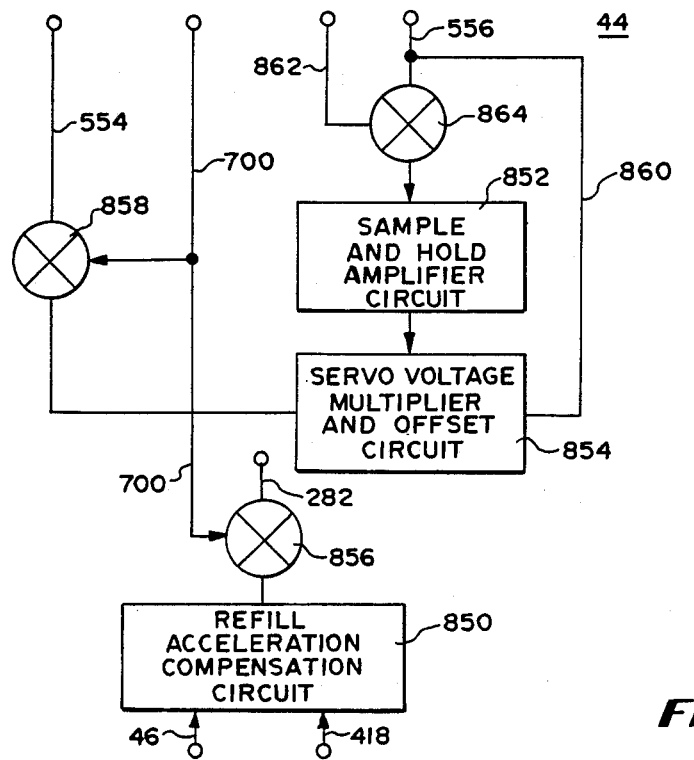
FIG. 26 is a block diagram of still another portion of the block diagram of FIG. 22.

In FIG. 26, there is shown a block diagram of the second compensation circuit 44 having a refill acceleration compensation circut 850, a sample and hold amplifier circuit 852 and a servo voltage multiplier and offset circuit 854. The refill acceleration compensation circuit 850 receives signals on conductor 46 indicating the flow rate and on conductor 418 from the compensation circuit and applies a signal to the ramp generator 278 (FIG. 9 and 16) through conductor 282 when a switch 856 is closed by a signal on conductor 700.

To apply a speed-up signal to the servo amplifier, conductor 700 is electrically connected to gate 858 to open this gate and apply the servo gain and compensation to the servo voltage multiplier and offset circuit 854. Upon receiving a signal indicating fluid delivery on conductor 862 from the delivery logic circuit 666 (FIG. 20), the switch 864 is closed to store the servo feedback signal from the output of the servo amplifier in the sample and hold amplifier circuit 852. The sample and hold amplifier circuit 852 is connected to the serve voltage multiplier and offset circuit 854 to be corrected and to apply the signal through gate 858 to the input 554 of the servoamplifier for acceleration.

Figure 27:
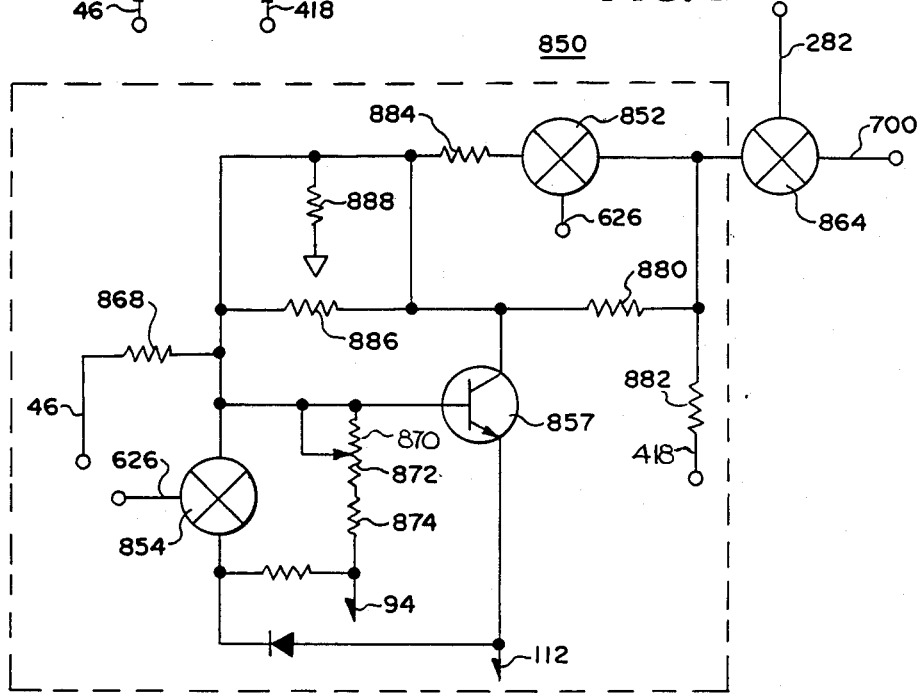
FIG. 27 is a block diagram of still another portion of the block diagram of the motor control system of FIG. 2.

In FIG. 27, there is shown a schematic circuit diagram of the refill acceleration compensation circuit 850 having a first analog switch 852, a second analog switch 854 and a 2N3704 NPN transistor 857. The transistor 857 applies a signal through switch 864 to conductor 282 to correct for the acceleration compensation with a compressibility correction being applied to its base. To apply an acceleration offset to the transistor 857 conductor 46 carrying the set point signal is electrically connected to: (1) the base of transistor 857 through a 10K resistor 868; (2) to the analog switch 854 through the resistor 868; (3) to a source 94 of a negative 12 volts through a 1K potentiometer gate 70, a 500 ohm resistor 872 and a 1K resistor 874 in series in the order named.

With this arrangement, the potentiometer gate 870 may be adjusted to provide different base current to the transistor 857. The emitter of the transistor 856 is electrically connected to a source of a negative 8 volts 112 and its collector is electrically connected to the source of the switch 864 through a 46.4K resistor 880 to provide a signal to the output conductor 282 upon receiving a signal on conductor 700. To provide compressibility compensation, conductor 418 is electrically connected to the switch 864 through a 1.8M resistor 882.

To provide a signal to conductor 520 to modify the rate of acceleration which commences at the start of refill when a low range signal is received on conductor 626 by the switches 852 and 854, conductor 46 is electrically connected to the source of the one level of switch 852 through: (1) the resistor 858 and a 24.9K resistor 884; (2) through the resistor 868, a 2.7K resistor 886 and the resistor 884. Conductor 46 is connected to the electrical common through the resistor 868 and a 649 ohm resistor 888.

Figure 28:
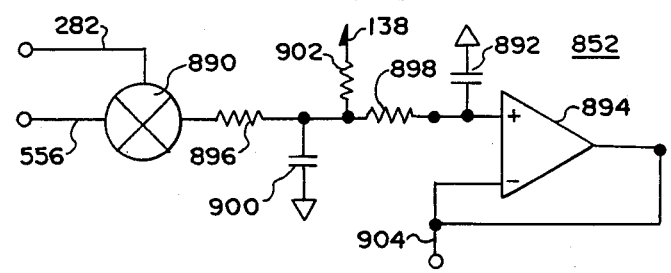
FIG. 28 is a schematic circuit diagram of a portion of the block diagram of FIG. 26.

In FIG. 28, there is shown a schematic of the sample and hold amplifier circuit 852 having a switch 890, a storage capacitor 892 and an operational amplifier 894. The switch 890 is electrically connected to the output of the servoamplifier through conductor 556 and to conductor 282 to receive a signal during the delivery portion of the pumping cycle. The switch 890 has one lead electrically connected to: (1) one plate of the 0.22 uf storage and noise filtering capacitor 892 through a 680K resistor 896 and a 3.3M resistor 898; (2) to the noninverting terminal of the amplifier 894 through the resistors 896 and 898; (3) to the electrical common through a 1 uf storage and noise filtering capacitor 900; and (4) to a source 138 of a positive 8 volts through the 22M resistor 902. The capacitor 892 is a 0.22 uf capacitor having one of its plates connected to the output of the switch 890 and its other connected to electrical ground. The capacitors 892 and 900 store a voltage representing the drive signal to the pump motor during the delivery portion of the pumping.

The output of the operational amplifier 894 is electrically connected to its inverting input terminal and to a conductor 904 from the servo voltage multiplier and offset circuit 854 (FIG. 26). With this circuit arrangement, a value of potential equivalent to the drive signal to the motor stored on capacitors 892 and 900 and applied with an offset to conductor 904 to the servo voltage multiplier and offset circuit 854.

Figure 29:
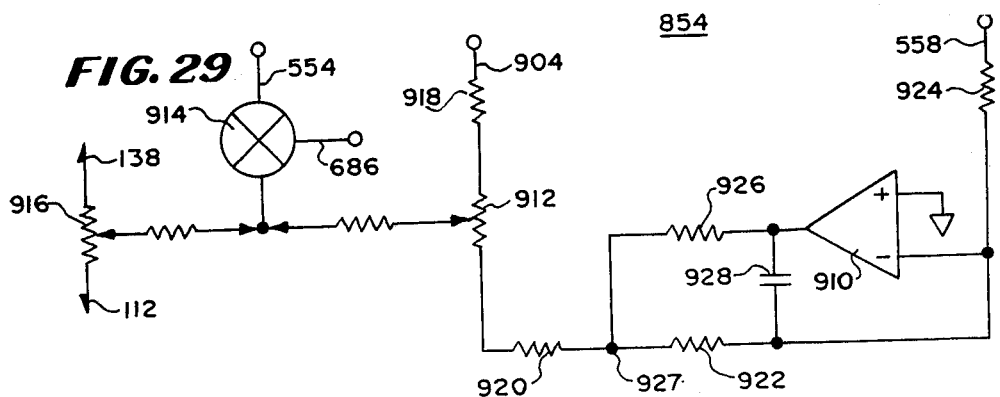
FIG. 29 is a schematic circuit diagram of still another protion of the block diagram of FIG. 26.

In FIG. 29, there is shown a schematic circuit diagram of the servo voltage multiplier and offset circuit 854 (FIG. 26) having an operational amplifier 910, a first potentiometer 912, an analog switch 914, and a second potentiometer 916. The potentiometer 916 is electrically connected at one end to a source 138 of a positive 8 volts and at the other end to a source 112 of a negative 8 volts to permit selection of a potential to be applied to the source of switch 914 and the potentiometer 912 is electrically connected at one end to conductor 904 of the sample and hold amplifier circuit 852 (FIGS. 26 and 28) through a 1K resistor 918.

The potentiometer 916 is a 10K potentiometer and the potentiomenter 912 is a 2K potentiometer. The other end of the potentiometer 912 is electrically connected through a 6.19K resistor 920 and a 100K resistor 922 to the inverting input terminal of the operational amplifier 910. The inverting input terminal of the operational amplifier 910 is also electrically connected to conductor 558 through a 100K resistor 924 to receive a signal from the output of the servoamplifier.

The output of the amplifier 910 is electrically connected through a 220 ohm resistor 926 to one side of the resistor 922 and through a 22 pf capacitor 928 to the other end of the resistor 922 and to the inverting input terminal of the amplifier 910. The noninverting input of the amplifier 910 is electrically connected to the electrical common so that the input signal from the output of the main servoamplifier on conductor 558 is applied to the inverting input terminal of the amplifier 910. The output of the amplifier 910 is applied to one end of the servo voltage multiplier where its magnitude is adjusted by the servo offset and servo voltage multiplier potentiometers and by the signal on conductor 904 for application through the switch 914 and conductor 554 to the input of the servoamplifier, thereby providing a feedback circuit which incorporates a sample and hold circuit and certain corrections.

When switch 914 closes and connects the wiper of potentiometer 912 to conductor 554, a negative signal from the sample and hold circuit at 904 is applied through the main servoamplifier 580 (FIG. 17) and inverted in amplifier 910. The signal is transmitted from conductor 904 on the output of the amplifier 894 (FIG. 28) in the sample and hold amplifier circuit 852 (FIGS. 26 and 28), through the potentiometer 912 and conductor 554 to the noninverting input of servoamplifier 580 (FIG. 17) and to the inverting input of operational amplifier 910. The amplifier 910 includes equal input and feedback resistors 922 and 924 establishing a potential at 927 on the output of the inverter 910 connecting resistors 920, 922 and 926 which is inverted but equal to the potential at 558.

The servoamplifier 580 (FIG. 17) is a high gain amplifier and causes the potential at 554 to be close to zero. Because amplifier 910 is a part of a negative 1 gain inverter, point 927 is the inverted value of the output of the servoamplifier at 558. Since the potential at the wiper of potentiometer 912 is not far from zero volts, being not far from the potential at 554, the potential at 927 is a multiple of the potential at 904 established by the voltage divider including the resistance from the wiper to the point 927 and from the wiper to point 904. The voltage at 927 is a multiple of the sample and hold voltage which is equivalent to the motor drive signal during delivery and the output signal at 558 is the inverted value of the potential at 927 to represent a multiple of the motor drive signal during delivery.

During acceleration, 686 goes high to close 914 connecting it to potentiometer 916. The offset on 916 is set to cause the servoamplifier to go negative when switch 914 closes. Voltages on 554 to servoamplifier, when switch 914 is closed, reaches a balance depending on potentiometer setting 912. With the arrangement, the servoamplifier generates a signal to cause acceleration of the motor until terminated by the acceleration time generator circuit, causing the total volume of fluid per stroke to tend to equalize and thus reduce pulsations of current through the chromatographic column. The acceleration is related to the signal on conductor 558 reflecting the sample and hold voltage stored during delivery.

Figure 30:
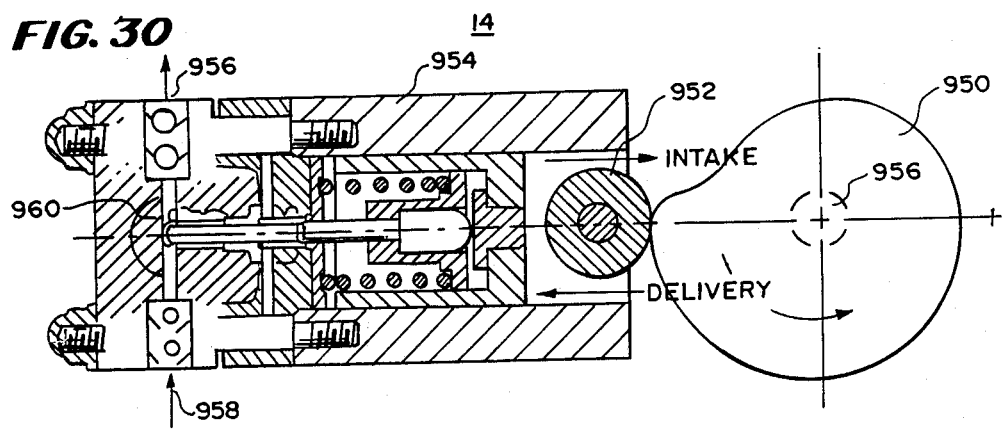
FIG. 30 is a sectional view, partly schematic of a pump in accordance with an embodiment of the invention.

In FIG. 30, there is shown a schematic sectional view of a pump 14 (FIG. 1) having a cam 950, a cam follower 952, and a pump head 954. The cam 950 is mounted to the output shaft of the motor 50 (FIG. 3) for rotation thereby. The cam follower 952 is mounted to move in the direction of the pump head 954 and the direction of the output shaft as the cam rotates to provide a reciprocating motion for a piston within the pump head 954.

The pump head 954 includes an outlet port 956 and an inlet port 958, closed by pressure-activated valves so that when the piston is moved inwardly in response to the cam follower 952, fluid is drawn into the cylinder 960, the outlet port 956 being closed and the inlet port 958 being open. Similarly, when the piston is moved forwardly, fluid is forced from the outlet port 956 and fluid is blocked from entering or leaving the inlet port 958 by check valves therein. The high pressure pump itself and the electric motor are not part of the invention themselves except that the rotatable masses thereof are sufficient to provide a flywheel effect to the pump itself. This and other flywheel implements reduce the effect of friction and increases repeatability. Bearings are selected for low friction.

Figure 31:
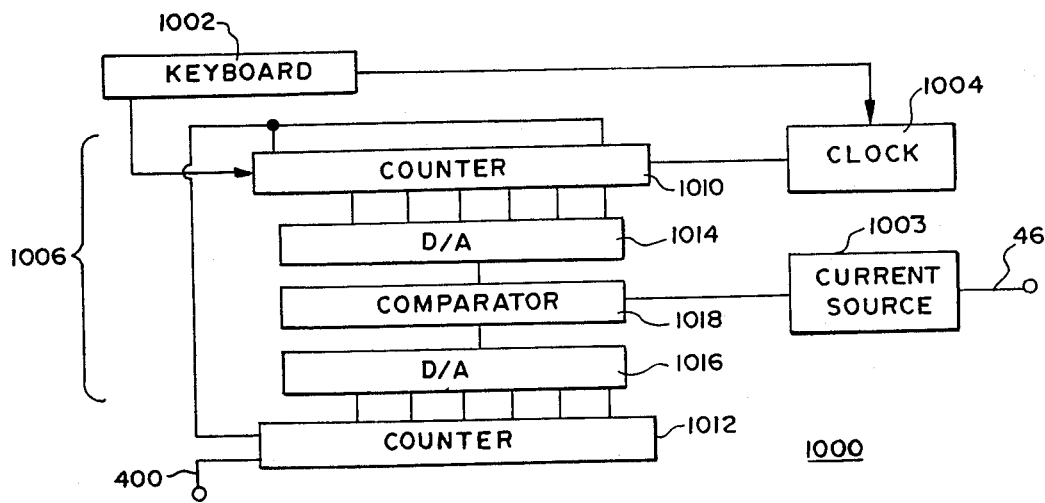
FIG. 31 is a schematic circuit diagram of an average rate of flow circuit.

In FIG. 31, there is shown a schematic circuit diagram of a circuit 1000 for presetting a liquid flow rate from the pump to adjsut the amplitude of the current on conductor 46 having a keyboard 1002, a clock source 1004, an updating circuit 1006, and a current source 1003. The current 46, of course, may be set by any analog circuit including a manual potentiometer in a manner known in the art.

In the preferred embodiment, it is set by a software program utilizing an 8031 microcomputer of the type manufactured by Intel, containing 128 bytes of RAM, a serial port and two counter/timers. An EPROM in the unit contains instruction codes for controlling the pump. The software program for monitoring the current 46 to maintain a constant average flow rate as follows:

MCS-S1 MACRO ASSEMBLER HPLC RECIP PUMP, 11.059 CRYSTAL AND SERIAL INSTALLED

| L00 | OBJ | LINE | SOURCE | | | |
|---|---|---|---|---|---|---|
| 03B9 | 22 | 763 | | RET | | ;TO MISS ONE IN TIMING ALSO |
| | | 764 | ; | | | |
| | | 765 | ; | CALCULATIONS FOR THE SECONDARY ADJUSTMENTS BASED ON EACH RATE | | |
| | | 766 | ; | JUMPED TO BY INTERRUPT | | |
| | | 767 | ; | BASEC CONTROL EQUATION IS: | | |
| | | 768 | ; | | | |
| | | 769 | ; | $DAC\_ADJUST1 = (DAC\_OLD * 833.3 * TIME)/(PULSES * FLOW\_BIN)$ | | |
| | | 770 | ; | $DAC\_OLD = DAC\_ADJUST1$ OF LAST READING | | |
| | | 771 | ; | | | |
| | | 772 | ; | WHERE SOME ADDED CONVERSION FACTORS ARE NEEDED | | |
| | | 773 | ; | AND PULSES 100 OR 300 AND TIME IS MEASURE, BUT NOT | | |
| | | 774 | ; | ACTUALLY STORED IN A REGISTER | | |
| | | 775 | ; | ADDITIONALLY, THE VALUES ARE LIMITED TO A ADJUSTMENT | | |
| | | 776 | ; | OF 2% AT .5 ML LINEARLY INCREASING TO 25% AT .01 ML | | |
| | | 777 | ; | | | |
| | | 778 | ; | | | |
| 03EA | C0D0 | 779 | CALC: | PUSH | PSW | ;PUSH RS0 AND RS1 WITH PSW |
| 03EC | D2D3 | 780 | | SETB | RS0 | |
| 03EE | D2D4 | 781 | | SETB | RS1 | |
| 03F0 | 902001 | 782 | | MOV | DPTR,#CO_1 | ;LOAD IN TIMER VALUE |
| 03F3 | E0 | 783 | | MOVX | A,BDPTR | |
| 03F4 | FD | 784 | | MOV | R5,A | |
| 03F5 | E0 | 785 | | MOVX | A,@DPTR | |
| 03F6 | FE | 786 | | MOV | R6,A | |
| 03F7 | 7F00 | 787 | | MOV | R7,#00H | |
| 03F9 | 900306 | 788 | | MOV | DPTR #NUMBER_OF_TIMES | |
| 03FC | E0 | 789 | | MOVX | A,@DPTR | |
| 03FD | 04 | 790 | | INC | A | |
| 03FE | F0 | 791 | | MOVX | @DPTR,A | ;PUT NUMBER BACK |
| 03FF | 203805 | 792 | | JB | A100_PULSES,CHK_15 | |
| 0402 | B40507 | 793 | | CONE | A,@05H,KEEP_COUNTING | |
| 0405 | 8014 | 794 | | SJMP | RESET_COUNTER | |
| 0407 | B40F02 | 795 | CHK_15: | CJNE | A,#0FH,KEEP_COUNTING | |
| 040A | 800F | 796 | | SJMP | RESET_COUNTER | |
| 040C | 203806 | 797 | KEEP_COUNTING: | JB | A100_PULSES,LOAD_ONLY_100 | |
| 040F | 71E0 | 798 | | ACALL | LOAD_OTHER_COUNTSA | |
| 0411 | 71C3 | 799 | | ACALL | LOADER0F300 | |
| 0413 | 800E | 800 | | SJMP | KEEP_COUNT_COUNTSA | |
| 0415 | 71E0 | 801 | LOAD_ONLY_100: | ACALL | LOAD_OTHER SD,8 — | |
| 0417 | 71CD | 802 | | ACALL | LOADER0F100 | |
| 0419 | 8008 | 803 | | SJMP | KEEP_COUNT | |
| 041B | 7400 | 804 | RESET_COUNTER: | MOV | A,#00H | |
| 041D | F0 | 805 | | MOVX | @DPTR,A | |
| 041E | 121770 | 806 | | LCALL | INIT_ADJUST | ;LOCATED RIGHT AFTER KRUN |
| 0421 | A1BE | 807 | | AJMP | CLEAR_OUT | ;GET OUT OF HERE |
| 0423 | 7AFF | 808 | KEEP_COUNT: | MOV | R2,#0FFH | ;LOAD IN 65535 (FFFF) |
| 0425 | 7BFF | 809 | | MOV | R3,#0FFH | |
| 0427 | 7C00 | 810 | | MOV | R4,#00H | |
| 0429 | B1D4 | 811 | | ACALL | BINSUB | ;SUBT 65535-COUNT_VALUE |
| 042B | AA20 | 812 | | MOV | R2,20H | |
| 042D | AB21 | 813 | | MOV | R3,21H | ;MULT BY 2560 |
| 042F | 7C00 | 814 | | MOV | R4,#00H | |
| 0431 | 7D00 | 815 | | MOV | R5,#00H | |
| 0433 | 7E0A | 816 | | MOV | R6,#0AH | |
| 0435 | 7F00 | 817 | | MOV | R7,#00H | |
| 03A4 | C24F | 708 | TO_MAIN: | CLR | START_UP | ;IF MADE IT THROUGH, THEN IS STARTED UP |
| 03A6 | 0201CB | 709 | | LJMP | MAIN | |
| | | 710 | ; | THE FOLLOWING SUBROUTINES (QUASI_INT, NO_PRESS UPDA, LOADEROFXXX, | | |
| | | 711 | ; | AND | | |
| | | 712 | ; | CALC ALL BELONG TO THE FLOW RATE ALORITHM, QUASI_INT IS USED | | |
| | | 713 | ; | WHEN THE | | |
| | | 714 | ; | INTERRUPTS HAVE BEEN DISABLED AND AFTER RENABLING, THE INTERRUPT BIT FOR | | |
| | | | | EXTERNAL IS SET, IT PULLS A "FAKE" INTERRUPT TO MAINTAIN THE ALGO, | | |
| | | 715 | ; | ALSO, THE SUBROUTINES ADJUST_REF, TAKE_CARE_HIGH, AND TAKE_CARE | | |
| | | 716 | ; | LOW | | |
| | | 717 | ; | ARE USED IN THE ALGORITHM AT DIFFERENT TIMES | | |
| | | 718 | ; | | | |
| 03A9 | 209605 | 719 | QUASI_INT: | JB | P1.6,CALL_CALC1 | |
| 03AC | D23C | 720 | | SETB | GATED | ;GATE OFF PRESSURE |
| 03AE | D23A | 721 | | SETB | GATED1 | ;MESSAGE TO OTHER LOOPS TO |
| 03B0 | 22 | 722 | | RET | | ;START INITIAL ALGORITHM MODE |
| 03B1 | 61EA | 723 | CALL_CALC1: | AJMP | CALC | ;RETURN IS IN CALC |
| | | 724 | ; | | | |
| | | 725 | ; | | | |
| | | 726 | ; | REAL INTERRUPTS FROM EXTERNAL JUMP TO THIS SPOT | | |

-continued

MCS-51 MACRO ASSEMBLER HPLC RECIP PUMP, 11.059 CRYSTAL AND SERIAL INSTALLED

| LOC | OBJ | LINE | SOURCE | | | |
|---|---|---|---|---|---|---|
| | | 727 | ; | | | |
| 03B3 | 209606 | 728 | NO_PRESS_UPDA: | JB | P1.6,CALL_CALC | |
| 03B6 | D23C | 729 | | SBTB | GATE0 | ;SET TO GATE OFF PRESSURE |
| 03B8 | D23A | 730 | | SETB | GATE1 | ;USED IN MAIN, RAPID, AND AGAIN |
| 03BA | 8002 | 731 | | SJMP | SKIDOO | |
| 03BC | 71EA | 732 | CALL_CALC: | ACALL | CALC | ;NOT A REFILL PULSE BUT A TIMER PULSE |
| 03B5 | D083 | 733 | SKIDOo: | FOP | DPH | |
| 03CO | D082 | 734 | | FOP | DFL | |
| 03C2 | 32 | 735 | | RETI | | |
| | | 736 | ; | | | |
| | | 737 | | | THESE ROUTINES LOAD THE TACH COUNTER (CO_2) | |
| | | 738 | ; | | | |
| | | 739 | | | | |
| 03C3 | 902002 | 740 | LOADEROF300: | MOV | DPTR,#CO_2 | |
| 03C6 | 742B | 741 | | MOV | A,#2BH | ;LOAD 299 SINCE FIRST PULSE LOADS IN |
| | | 742 | | | | ;THE COUNT VALUE AND SO IS MISSED |
| 03C6 | F0 | 743 | | MOVX | @DPTR,A | ; |
| 03C9 | 7401 | 744 | | MOV | A,#01H | ; |
| 03C8 | F0 | 745 | | MOVX | @DPTR,A | |
| 03CO | 22 | 746 | | RET | | |
| 03CD | 902002 | 747 | LOADEROF100: | MOV | DPTR,#CO_2 | |
| 03D0 | 7463 | 748 | | MOV | A,#063H | ;LOAD IN 99 FOR SAME REASON AS 300 |
| 03D2 | F0 | 749 | | MOVX | @DPTR,A | |
| 03D3 | 7400 | 750 | | MOV | A,#00H | |
| 03d5 | F0 | 751 | | MOVX | @DPTR,A | |
| 03D6 | 22 | 752 | | RET | | |
| 03B7 | 902000 | 753 | LOAD_OTHER_COUNTS: | MOV | DPTR,#CO_C | |
| 03D8 | 74BA | 754 | | MOV | A,#0EAH | ;LOAD DO_C WITH 17,658 |
| 03BC | F0 | 755 | | MOVX | @DPTR,A | ;TIMERS LINKED TO 32 BITS |
| 03DD | 7445 | 756 | | MOV | A,#45H | |
| 03DF | F0 | 757 | | MOVX | @DPTR,A | |
| 03E0 | 902001 | 758 | LOAD_OTHER_COUNTSA: | MOV | DPTR,#CO_1 | |
| 03E3 | 74FD | 759 | | MOV | A,#0FDH | ;SO CO_1 COUNTS AT .01SEC |
| 03E3 | F0 | 760 | | MOVX | @DPTR,A | ;DOWN FROM 65533 |
| 03E6 | 74FF | 761 | | MOV | A,#0FFH | ;65533 SINCE FIRST PULSE LOADS |
| 03E8 | F0 | 762 | | MOVX | @DPTR,A | ;VALUE AND IS MISSED AND SEEMS |
| 0437 | B1E8 | 818 | | ACALL | BINMUL | |
| 0439 | AA23 | 819 | | MOV | R2,23H | |
| 043B | AB24 | 820 | | MOV | R3,24H | |
| 043D | AC25 | 821 | | MOV | R4,25H | |
| 043F | 203816 | 822 | | JB | A100_PULSES,ONLY_100 | |
| 0442 | 7D46 | 823 | | MOV | R5,#46H | ;ADD 1282=502H (RNDING IN NEXT) |
| 0444 | 7E05 | 824 | | MOV | R6,#05H | ;12/2/85 ADD 1350=546H |
| 0446 | 7F00 | 825 | | MOV | R7,#00H | |
| 0446 | B1C1 | 826 | | ACALL | BINADD | |
| 044A | AA20 | 827 | | MOV | R2,20H | |
| 044C | AB21 | 828 | | MOV | R3,21H | ;*12/2/85 CNG REF TO 833.3* |
| 044E | AC22 | 829 | | MOV | R4,22H | |
| 0450 | 7D8C | 830 | | MOV | R5,#06CH | ;DIVBY 2563=A03H=(300*7500/878) |
| 0452 | 7E0A | 831 | | MOV | R6,#0AH | ;WHERE 7500 IS 2000UL REF WORD |
| 0454 | 7F00 | 832 | | MOV | R7,#00H | ;*12/2/85 (300*7500/833.3)=2700 |
| 0456 | 8014 | 833 | | SJMP | CALL_DIVIDER | ;2700=A8CH |
| 0458 | 7DC2 | 834 | ONLY_100: | MOV | R5,#0C2H | ;ADD 427 FOR ROUNDING (854/2) |
| 045A | 7B01 | 835 | | MOV | R6,#01H | ;427=1ABH |
| 045C | 7F00 | 836 | | MOV | R7,#00H | ;**12/2/85 450=1C2H=(900/2) |
| 045B | B1C1 | 837 | | ACALL | BINADD | |
| 0460 | AA20 | 838 | | MOV | R2,20H | |
| 0462 | AB21 | 839 | | MOV | R3,21H | |
| 0464 | AC22 | 840 | | MOV | R4,22H | |
| 0466 | 7D84 | 841 | | MOV | R5,#084H | |
| 0468 | 7B03 | 842 | | MOV | R6,#03H | ;DIVBY 854=356H=(100*7500/878) |
| 046A | 7F00 | 843 | | MOV | R7,#00H | ;**12/2/85 900=384H=(100*7500/833.3) |
| 046D | D1AD | 844 | CALL_DIVIDER: | ACALL | BINDIV | |
| 046E | AA20 | 845 | | MOV | R2,20H | ;GET RESULT |
| 0470 | AB21 | 846 | | MOV | R3,21H | |
| 0472 | AC22 | 847 | | MOV | R4,22H | |
| 0474 | 205206 | 848 | | JB | CALIBRATED,DIVOTHER | |
| 0477 | AD46 | 849 | | MOV | R5,FLOW_BIN | ;MULTIPLY BY FLOWRATE BINARY FORM (0 TO 187 |
| | | | 5 BINARY FOR 0 TO 500 UL/MIN) | | | |
| 0479 | AE47 | 850 | | MOV | R6,FLOW_BIN+1 | |
| 047B | 8004 | 851 | | SJMP | DIV_NORM | |
| 0470 | AD5F | 852 | DIVOTHER: | MOV | R5,FLOW_BIN_CAL | ;IF CALIBRATED, USE THIS # |
| 047F | AE60 | 853 | | MOV | R6,FLOW_BIN_CAL+1 | |
| 0481 | 7F00 | 854 | DIV_NORM: | MOV | R7,#00H | |
| 0483 | B1E8 | 855 | | ACALL | BINMUL | |
| 0485 | AA23 | 856 | | MOV | R2,23H | ;ADD 50 FOR DIVISION ROUNDING |

-continued
MCS-S1 MACRO ASSEMBLER HPLC RECIP PUMP, 11.059 CRYSTAL AND SERIAL INSTALLED

| L00 | OBJ | LINE | SOURCE | | |
|---|---|---|---|---|---|
| 0487 | AB24 | 857 | MOV | R3,24H | |
| 0489 | AC25 | 858 | MOV | R4,25H | |
| 048B | 7D32 | 859 | MOV | R5,#50 | |
| 048D | 7B00 | 860 | MOV | R6,#00 | |
| 048F | 7F00 | 861 | MOV | R7,#00 | |
| 0491 | B1C1 | 862 | ACALL | BINADD | |
| 0493 | AA20 | 863 | MOV | R2,20H | ;DIVIDE BY 100 |
| 0495 | AB21 | 864 | MOV | R3,21H | |
| 0497 | AC22 | 865 | MOV | R4,22H | |
| 0499 | 7D64 | 866 | MOV | R5,#064H | |
| 049B | 7E00 | 867 | MOV | R6,#00H | |
| 049D | 7F00 | 868 | MOV | R7,#00H | |
| 049E | D1AD | 869 | ACALL | BINDIV | |
| 04A1 | AA20 | 870 | MOV | R2,20H | |
| 04A3 | AB21 | 871 | MOV | R3,21H | |
| 04A5 | AC22 | 872 | MOV | R4,22H | |
| 04A7 | AD59 | 873 | MOV | R5,DAC_ADJUST1 | |
| 04A9 | AE5A | 874 | MOV | R6,DAC_ADJUST1+1 | |
| 04AB | 7F00 | 875 | MOV | R7,#00H | |
| 04AD | B1E8 | 876 | ACALL | BINMUL | ;MULTIPLY OLD BY CURRENT# |
| 04AF | 7F00 | 877 | MOV/ R7,#00H | | |
| 04B1 | AA23 | 878 | MOV | R2,23H | |
| 04B3 | AB24 | 879 | MOV | R3,24H | |
| 04B5 | AC25 | 880 | MOV | R4,25H | |
| 04B7 | 7D00 | 881 | MOV | R5,#00H | |
| 04B9 | 7E05 | 882 | MOV | R6,#05H | |
| 04BB | 7F00 | 883 | MOV | R7,#00H | |
| 04BD | B1C1 | 884 | ACALL | BINADD | ;ADD 1280 FOR ROUNDING |
| 04BF | AA20 | 885 | MOV | R2,20H | ;DIVIDE BY 2560 BY MOVING OVER |
| 04C1 | AB21 | 886 | MOV | R3,21H | ;ONE BYTE WHEN STORING |
| 04C3 | AC22 | 887 | MOV | R4,22H | |
| 04C5 | 7D00 | 888 | MOV | R5,#00H | |
| 04C7 | 7E0A | 889 | MOV | R6,#0AH | |
| 04C9 | 7F00 | 890 | MOV | R7,#00H | |
| 04CB | D1AD | 891 | ACALL | BINDIV | |
| 04CD | AA20 | 892 | MOV | R2,20H | |
| 04CF | AB21 | 893 | MOV | R3,21H | |
| 04D1 | AC22 | 894 | MOV | R4,22H | |
| 04D3 | 900300 | 895 | MOV | DPTR,#DAC_OLD | |
| 04D6 | E559 | 896 | MOV | A,DAC_ADJUST1 | |
| 04D8 | F0 | 897 | MOVX | @DPTR,A | |
| 04D9 | A3 | 898 | INC | DPTR | |
| 04DA | E55A | 899 | MOV | A,DAC_ADJUST1+1 | |
| 04DC | F0 | 900 | MOVX | @DPTR,A | |
| 04DD | AD59 | 901 | MOV | R5,DAC_ADJUST1 | |
| 04DF | AE5A | 902 | MOV | R6,DAC_ADJUST1+1 | |
| 04E1 | 8A59 | 903 | MOV | DAC_ADJUST1,R2 | ;MOV NEW IN DAC_ADJUST |
| 04E3 | 8B5A | 904 | MOV | DAC_ADJUST1+1,R3 | |
| 04E5 | B1D4 | 905 | ACALL | BINSUB | ;SUBT NEW FROM OLD |
| 04E7 | 4069 | 906 | JC | BEELOW | ;CARRY THEN ADJUST IS BELOW REF |
| 04E9 | 7A75 | 907 | MOV | R2,#75H | ;USE 102+885/FLOW_BIN AS LIMIT |
| 04EB | 7B03 | 908 | MOV | R3,#03H | |
| 04ED | 7C00 | 909 | MOV | R4,#00 | |
| 04EF | AD46 | 910 | MOV | R5,FLOW_BIN | |
| 04F1 | AE47 | 911 | MOV | R6,FLOW_BIN+1 | |
| 04F3 | 7F00 | 912 | MOV | R7,#00 | |
| 04F5 | 1206AD | 913 | LCALL | BINDIV | |
| 04F8 | AA20 | 914 | MOV | R2,20H | |
| 04FA | AB21 | 915 | MOV | R3,21H | |
| 04FC | AC22 | 916 | MOV | R4,22H | |
| 04FE | 7D66 | 917 | MOV | R5,#102 | |
| 0500 | 7E00 | 918 | MOV | R6,#00 | |
| 0502 | 7F00 | 919 | MOV | R7,#00 | |
| 0504 | 1205C1 | 920 | LCALL | BINADD | |
| 0507 | AD20 | 921 | MOV | R5,20H | |
| 0509 | AE21 | 922 | MOV | R6,21H | |
| 050B | AF22 | 923 | MOV | R7,23H | |
| 050D | 900300 | 924 | MOV | DPTR,#DAC_OLD | |
| 0510 | E0 | 925 | MOVX | A,@DPTR | ;LOAD OLD NUMBER TO MAKE 2% LIM |
| 0511 | FA | 926 | MOV | R2,A | |
| 0512 | A3 | 927 | INC | DPTR | |
| 0513 | E0 | 928 | MOVX | A,@DPTR | |
| 0514 | FB | 929 | MOV | R3,A 00H | |
| 0515 | 7C00 | 930 | MOV | R4,#00H | |
| 0517 | 1205E8 | 931 | LCALL | BINMUL | |
| 051A | AA23 | 932 | MOV | R2,23H | ;DIVIDE BY 100 |
| 051C | AB24 | 933 | MOV | R3,24H | ;ADD 50 FIRST FOR ROUNDING |
| 051E | AC25 | 934 | MOV | R4,25H | |
| 0520 | 7D32 | 935 | MOV | R5,#50 | |

-continued

MCS-S1 MACRO ASSEMBLER HPLC RECIP PUMP, 11.059 CRYSTAL AND SERIAL INSTALLED

| L00 | OBJ | LINE | SOURCE | | | |
|---|---|---|---|---|---|---|
| 0522 | 7E00 | 936 | | MOV | R6,#00H | |
| 0524 | 7F00 | 937 | | MOV | R7,#00H | |
| 0526 | B1C1 | 938 | | ACALL | BINADD | |
| 0528 | AA20 | 939 | | MOV | R2,20H | |
| 052A | AB21 | 940 | | MOV | R3,21H | |
| 052C | AC22 | 941 | | MOV | R4,22H | |
| 052E | 7D64 | 942 | | MOV | R5,#100 | |
| 0530 | 7E00 | 943 | | MOV | R6,#00 | |
| 0532 | 7F00 | 944 | | MOV | R7,#00 | |
| 0534 | D1AD | 945 | | ACALL | BINDIV | |
| 0536 | A820 | 946 | | MOV | R0,20H | ;STORE IN TWO PLACES |
| 0538 | A921 | 947 | | MOV | R1,21H | |
| 053A | AA20 | 948 | | MOV | R2,20H | |
| 053C | AB21 | 949 | | MOV | R3,21H | |
| 053E | AC22 | 950 | | MOV | R4,22H | |
| 0540 | AD59 | 951 | | MOV | R5,DAC_ADJUST1 | |
| 0542 | AE5A | 952 | | MOV | R6,DAC_ADJUST1+1 | |
| 0544 | 7F00 | 953 | | MOV | R7,#00H | |
| 0546 | B1D4 | 954 | | ACALL | BINSUB | ;SUBSTRACT NEW FROM 2+% VALUE |
| 0548 | 4002 | 955 | | JC | TIMES_102 | ;IF CARRY THEN USE 2+% VALUE |
| 054A | 806A | 956 | | SJMP | DACCY | |
| 054C | 8859 | 957 | TIMES_102: | MOV | DAC_ADJUST1,R0 | |
| 054E | 895A | 958 | | MOV | DAC_ADJUST1+1,R1 | ;LOAD IN 2+% VAL |
| 0550 | 8064 | 959 | | SJMP | DACCY | |
| 0552 | 7A75 | 960 | BEELOW: | MOV | R2,#75H | |
| 0554 | 7B03 | 961 | | MOV | R3,#03H | |
| 0556 | 7C00 | 962 | | MOV | R4,#00H | |
| 0556 | AD46 | 963 | | MOV | R5,FLOW_BIN | |
| 055A | AE47 | 964 | | MOV | R6,FLOW_BIN+1 | |
| 055C | 7F00 | 965 | | MOV | R7,#00H | |
| 055E | 1206AD | 966 | | LCALL | BINDIV | |
| 0561 | AD20 | 967 | | MOV | R5,20H | |
| 0563 | AE21 | 968 | | MOV | R6,21H | |
| 0565 | AF22 | 969 | | MOV | R7,22H | |
| 0567 | 7A62 | 970 | | MOV | R2,#98 | |
| 0569 | 7B00 | 971 | | MOV | R3,#00H | |
| 056B | 7C00 | 972 | | MOV | R4,#00H | |
| 056D | 1205D4 | 973 | | LCALL | BINSUB | |
| 0570 | AD20 | 974 | | MOV | R5,20H | ;MULT BY 98-885/FLOW_BIN |
| 0572 | AB21 | 975 | | MOV | R6,21H | ;WILL DIVIDE BY 100 TO GET A |
| 0574 | 7F00 | 976 | | MOV | R7,#00H | ;2+PERCENT LIMIT TO CHECK WITH |
| 0576 | 900300 | 977 | | MOV | DPTR,#DAC_OLD | |
| 0579 | E0 | 978 | | MOVX | A,@DPTR | |
| 057A | FA | 979 | | MOV | R2,A | |
| 057B | A3 | 980 | | INC | DPTR | |
| 057C | B0 | 981 | | MOVX | A,@DPTR | |
| | | 1750 | ADJUSTER: | ;THIS SUBROUTINE PREPARES THE TIMER (8253) | | |
| | | 1751 | | ;FOR THE NEXT PART OF THE CONTROL ALGORITHM | | |
| | | 1752 | | | | |
| | | 1753 | | | | |
| 0B38 | 7A40 | 1754 | | MOV | R2,#40H | ;WAIT 40,000 CYCLES BEFORE CHECK |
| 0B3A | 7B9C | 1755 | | MOV | R3,#9CH | ;EQUIVALENT TO .08 SEC |
| 0B3C | DAFE | 1756 | ZEROSA: | DJNZ | R2,ZEROSA | |
| 0B3E | DBFC | 1757 | | DJNZ | R3,ZEROSA | |
| 0B40 | 30B311 | 1758 | | JNB | R3,3,NOADJUST | ;IF STILL GATED, DISREGARD |
| 0B43 | C23A | 1759 | | CLR | GATED1 | ;GATE INTERRUPT HAS BEEN HANDELED |
| 0B45 | 20640C | 1760 | | JB | PREP_HEAD,NOADJUST | ;NOADJUSTMENTS FOR PREP |
| 0B48 | 307D09 | 1761 | | JNB | MICROL,NOADJUST | ;OR FOR HIGH FLOWS |
| 0B4B | E531 | 1762 | | MOV | A,FLOW_RATE+1 | |
| 0B4D | B40502 | 1763 | | CJNE | A,#05H,CHK_FURTHER | ;ADJUSTS UP TO 499 UL/MIN |
| 0B50 | 8002 | 1764 | | SJMP | NOADJUST | |
| 0B52 | 4001 | 1765 | CHK_FURTHER | JC | OK | |
| 0B54 | 22 | 1766 | NOADJUST: | RET | | |
| 0B55 | E531 | 1767 | OK: | MOV | A,FLOW_RATE+1 | ;READJUST FOR NEXT UPDATES |
| 0B57 | B40103 | 1768 | | CJNE | A,#01H,IS_LOWER | ;IS IT LESS THAN 100UL |
| 0B5A | 020B5F | 1769 | | JMP | NO_SET | |
| 0B5D | 4004 | 1770 | IS_LOWER: | JC | SET_IT_HI | ;IF IS, USE 100 PULSES |
| 0B5F | C238 | 1771 | NO_SET: | CLR | A100_PULSES | |
| 0B61 | 8010 | 1772 | | SJMP | LOAD_300 | |
| 0B63 | D238 | 1773 | SET_IT_HI: | SETB | A100_PULSES | |
| 0B65 | 1203D7 | 1774 | | LCALL | LOAD_OTHER_COUNTS | |
| 0B68 | 1203CD | 1775 | | LCALL | LOADEROF100 | |
| 0B6B | 900306 | 1776 | | MOV | DPTR,#NUMBER_OF_TIMES | |
| 0B6E | 7400 | 1777 | | MOV | A,#00H | ;CLEAR THIS |
| 0B70 | F0 | 1778 | | MOVX | @DPTR,A | |
| 0B71 | 800C | 1779 | | SJMP | SET_CLOCK_COUNT | |
| 0B73 | 1203D7 | 1780 | LOAD_300: | LCALL | LOAD_OTHER_COUNTS | |

-continued

MCS-S1 MACRO ASSEMBLER HPLC RECIP PUMP, 11.059 CRYSTAL AND SERIAL INSTALLED

| L00 | OBJ | LINE | SOURCE | | | |
|---|---|---|---|---|---|---|
| 0B76 | 1203C3 | 1781 | | LCALL | LOADEROF300 | |
| 0B79 | 900306 | 1782 | | MOV | DPTR,#NUMBER_OF_TIMES | |
| 0B7C | 7400 | 1783 | | MOV | A,#00H ; | |
| 0B7E | F0 | 1784 | | MOVX | @DPTR,A | |
| 0B7F | D296 | 1785 | SET_CLOCK_COUNT: | SETB | P1.6 | |
| 0B81 | 22 | 1786 | | RET | | |
| | | 1787 | ; | | | |
| | | 1788 | ; | | | |
| | | 1789 | ; | | | |
| | | 1790 | ; | | | |
| | | 1791 | ; | BRANCH ON KEYBOARD ENTRY | | |
| | | 1792 | ; | | | |
| 0B82 | 12168E | 1793 | KEYBD: | LCALL | BOP | |
| 0B85 | 900801 | 1794 | | MOV | DPTR,#DISPLAY_CONTROL | |
| 0B88 | 7440 | 1795 | | MOV | A,#40H ;READ KEYBOARD | |
| 0B8A | F0 | 1796 | | MOVX | @DPTR,A | |
| 0B8B | A3 | 1797 | | INC | DPTR | |
| 0B8C | E0 | 1798 | | MOVX | A,@DPTR | |
| 0B8D | 23 | 1799 | | RL | A | |
| 0B8E | 547E | 1800 | | ANL | A,1π01111110B | ;MASK ACTIVE KEYS |
| 0B90 | F8 | 1801 | | MOV | R0,A | ;SAVE COPY |
| 0B91 | 900B9D | 1802 | | MOV | DPTR,#ADTABLE | |
| 0B94 | 04 | 1803 | | INC | A | |
| 0B95 | 93 | 1804 | | MOVC | A,@A+DPTR | ;CREATE RETURN ADDRESS |
| 057D | FB | 982 | | MOV | R3,A | |
| 057E | 7C00 | 983 | | MOV | R4,#00H | |
| 0580 | B1E8 | 984 | | ACALL | BINMUL | |
| 0582 | AA23 | 985 | | MOV | R2,23H | ;DIVIDE BY 100 |
| 0584 | AB24 | 986 | | MOV | R3,24H | ;ADD 50 FIRST FOR ROUNDING |
| 0586 | AC25 | 987 | | MOV | R4,25H | |
| 0588 | 7D32 | 988 | | MOV | R5,#50 | |
| 058A | 7E00 | 989 | | MOV | R6,#00H | |
| 058C | 7F00 | 990 | | MOV | R7,#00 | |
| 058E | B1C1 | 991 | | ACALL | BINADD | |
| 0590 | AA20 | 992 | | MOV | R2,20H | |
| 0592 | AB21 | 993 | | MOV | R3,21H | |
| 0594 | AC22 | 994 | | MOV | R4,22H | |
| 0596 | 7D64 | 995 | | MOV | R5,#100 | |
| 0598 | 7E00 | 996 | | MOV | R6,#00 | |
| 059A | 7F00 | 997 | | MOV | R7,#00 | |
| 059C | D1AD | 998 | | ACALL | BINDIV | |
| 059E | A820 | 999 | | MOV | R0,20H | ;STORE IN TOW PLACES |
| 05A0 | A921 | 1000 | | MOV | R1,21H | |
| 05A2 | AA20 | 1001 | | MOV | R2,20H | |
| 05A4 | AB21 | 1002 | | MOV | R3,21H | |
| 05A6 | AC22 | 1003 | | MOV | R4,22H | |
| 05A8 | AD59 | 1004 | | MOV | R5,DAC_ADJUST1 | |
| 05AA | AE5A | 1005 | | MOV | R6,DAC_ADJUST1+1 | |
| 05AC | 7F00 | 1006 | | MOV | R7,#00H | |
| 05AE | B1D4 | 1007 | | ACALL | BINSUB | ;SUBSTRACT NEW FROM 2% VALUE |
| 05B0 | 4004 | 1008 | | JC | DACCY | ;IF CARRY THEN USE OLD VALUE |
| 05B2 | 8859 | 1009 | | MOV | DAC_ADJUST1,R0 | |
| 05B4 | 895A | 1010 | | MOV | DAC_ADJUST1+1,R1 | |
| 05B6 | 7959 | 1011 | DACCY: | MOV | R1,#DAC_ADJUST1 | |
| 05B8 | 901000 | 1012 | | MOV | DPTR,#ANALOG_LO | |
| 05BB | 1214DC | 1013 | | LCALL | DAC5 | |
| 05BE | D0D0 | 1014 | CLEAR OUT: | POP | PSW | ;RETURN RBANK SELECTS |
| 05C0 | 22 | 1015 | | RET | | ;RETURN TO INT HANDLE |
| | | 1016 | | | | ;OR TO CALLING SUBROUTINE |
| | | 1017 | | | | ;IF NOT AN ACTUAL INTERRUPT |
| | | 1018 | | | | |
| | | 1019 | | | | |
| | | 1020 | | | | |
| | | 1021 | ; | | | |
| | | 1022 | ; | | | |
| | | 1023 | ;********** BINARY NUMBER MATH ROUTINES ********** | | | |
| | | 1024 | ; | | | |
| | | 1025 | ;W+X=Y W−X=Y W/X=YZ W*X=YZ | | | |
| | | 1026 | ; | | | |
| | | 1027 | ; | | | |
| 05C1 | E51A | 1028 | BINADD: | MOV | A,01AH | |
| 05C3 | 251D | 1029 | | ADD | A,01DH | |
| 05C5 | F520 | 1030 | | MOV | 20H,A | |
| 05C7 | E51B | 1031 | | MOV | A,1BH | |
| 05C9 | 351E | 1032 | | ADDC | A,1EH | |
| 05CB | F521 | 1033 | | MOV | 21H,A | |
| 05CD | E51C | 1034 | | MOV | A,1CH | |
| 05CF | 351F | 1035 | | ADDC | A,1FH | |

| | | MCS-S1 MACRO ASSEMBLER HPLC RECIP PUMP, 11.059 CRYSTAL AND SERIAL INSTALLED | | | |
|---|---|---|---|---|---|
| L00 | OBJ | LINE | SOURCE | | |
| 05D1 | F522 | 1036 | | MOV | 22H,A |

In addition to a source which may be adjusted by a potentiometer and the use of a computer as is done in the preferred embodiment, a hardward circuit may be used as shown in FIG. 1 in which a keyboard 1002 initiates clock pulses from a source 1004 and a value into the updating circuit 1006. A source of pulses from the tachometer is applied through conductor 400 to the updating circuit and the number of tachometer pulses in one cycle of the pump are counted sequentially and compared with an idealized number, with the current course being increased if the number lags so that the computer averages the amount of flow across a cycle of the pump to maintain a constant average flow rate by admusting the current source in addition to the other adjustments hereinbefore described.

To monitor the tachometer pulses, the updating circuit includes first and second counters 1010 and 1012, first and second digital-to-analog converters 1014 and 1016 and a comparator 1018. The counter 1010 has counted into it from the clock 1004 the clock pulses in a cycle of the pump before being reset and the clock rate is set to equal the number of tachometer pulses which should be received in one pump cycle. The counter 1012 is reset by the same pulse that resets the counter 1010 but counts the tachometer pulses as they actually occur. Digital-to-analog converter 1014 generates an analog voltage equivalent to the counts in counter 1010 and digital-to-analog converter 1016 generates an analog signal equivalent to the counts of counter 1012. The comparator 1018 compares the analog outputs from the digital-to-analog converters 1014 and 1016 and adjusts the current source 1003 with the signal so as to maintain a signal on conductor 46 which will compensate for deviations of flow from the pump from cycle to cycle.

Before operating the pump, it is calibrated to avoid cavitation while the motor accelerates from the start of a refill cycle to pull fluid into the pump until a predetermined period of time has elapsed from the start of the acceleration. This is accomplished by adjusting potentiometers 916 and 912 (FIG. 29), 514 (FIG. 15) and 857 (FIG. 27) while pumping water and monitoring the pressure output from stroke to stroke to detect cavitation. The values, which affect the acceleration, when properly set reduce the cavitation and variation in flow rate with pressure variations and may be maintained for maximum operation of the pump.

Once the pump is calibrated, it is operated by setting a flow rate, priming the pump, filling its cylinder and expelling fluid. In expelling the fluid, near an end portion of the stroke, the pump is run at a constant speed until it reaches the end of the expulsion stroke, at which time a refill signal is generated and the piston begins a refill stroke in a return direction. When it reaches a start of the refill stroke, the pump motor begins to accelerate at the controlled rate and continues to accelerate for a predetermined amount of time related to the operating conditions, at which time it slows to the preset rate for constant flow.

In setting a flow rate in the preferred embodiment, the flow rate is keyed into the keyboard and a software circuit retains it, generating a set point signal for application to an analog voltage generator of a conventional type. The analog set point signal controls the flow rate.

The preset flow rate is compared with tachometer pulses generated during the forward stroke of the piston of the pump and, if the average pumping rate is below that preset, the voltage on conductor 46 is increased.

Although a computer is used for this function in the preferred embodiment, it can be accomplished by a hardware circuit such as that shown in FIG. 31 in which a count representing an ideal tachometer rate is set into a counter 1010 (FIG. 31) and converted to a digital-to-analog signal in the digital-to-analog converter 1014. The tachometer pulses as they are counted on conductor 400 are also converted to an analog signal in digital-to-analog converter 1016 and the analog signals are compared to adjust the current source so that a basic linear feedback circuit related to liquid influent flow into the chromatographic column and injector system 18 (FIG. 1) is provided.

Of course, the current for conductor 46 may be set by a simple source of potential and variable resistor or by any other technique in which a current directly proportional to the flow rate is provided. This current will, in general, control through a linear circuit the flow rate regardless of how it is obtained and exert a tendency to maintain it constant as influent to the chromatographic column.

During a refill cycle and the first part of the cycle forcing fluid out of the pump, the motor 50 (FIG. 3) receives a signal from the nonlinear flow rate control circuit 42 (FIG. 2 and 9) having a time duration controlled by a timer and initiated at a point during the refill cycle and continuing for a time thereafter related to rate of flow which has been set for flow into the chromatographic column. The time of acceleration is related to the charge on capacitor 150 (FIG. 5) which is modulated by transistor 716 (FIG. 23) in response partly to the signal on conductor 46 (FIG. 23) from the set point value. The amount of acceleration is related to the closed loop servo signal which was last driving the pump, that value being obtained by a sample and hold circuit electrically connected to the output of the servo amplifier to store the signal during the last part of a pumping cycle when the pump is pumping at a constant rate under closed loop control of a motor speed rotation signal. The sample and hold amplifier circuit (FIGS. 26 and 28) stores a signal on a capacitor 900 and 892 (FIG. 28). The rate of acceleration is adjusted by offset and multiplication values during calibration by adjusting potentiometers 916 and 912. The signal from potentiometer 912 is applied as a closed loop control signal to the amplifier 580 (FIG. 17) in which the feedback signal has been closed by analog switch 914 and the amplifier 910.

With this arrangement, the pump is maintained during a portion of a pumping cycle at a constant speed under a tachometer feedback circuit using analog circuitry and a digital control which adusts the constant current control for the flow rate. During the refill cycle, the motor is accelerated continuously while the piston is controlled by a cam to accelerate and decelerate to zero and then accelerate again, with the motor acceleration terminating at a time controlled by a timer to reduce pulsations in flow to a minimum.

From the above description, it can be understood that the pump of this invention has several advantages, such as: (1) the time during which no liquid is pumped through the outlet port is low; (2) the pump is relatively uncomplicated because the acceleration time of the motor is time-limited rather than distance limited; (3) the pump is able to accomodate a wider range of flow rates without cavitation; (4) the pump maintains an accelerating velocity during the return portion while refilling coming to a stop at the end and accelerating upwardly under constant positive driving of a motor through a cam, with the motor receiving a continuous accelerating voltage so as to reduce noise which might otherwise be caused by inertial effects as the motor speed is changed; (5) the average flow rate is continuously monitored and adjusted by adjusting a current input signal representing the preset flow rate of fluid; and (6) the flow rate remains constant as pressure varies.

Although a preferred embodiment of the invention has been described with some particularity, many modifications and variations are possible in the preferred embodiment without deviating from the invention. Therefore, it is to be understood that, with the scope of appended claims, the invention may be practiced other than as specifically described.

What is claimed is:

1. A liquid chromatographic system comprising:
    pump motor means;
    a chromatographic column;
    means for controlling the speed of the pump motor means in a first time period at a rate which results in a constant flow rate into the chromatographic column and for controlling the speed of the pump motor means in a second time period at a rate which avoids cavitation during refilling of the pump and which accelerates with time for a time period that is related to the rate of pumping during at least a portion of the first time period; wherein said pump motor means runs in cycles having a pumping cycle portion and a refilling cycle portion with the duration of the first time period being related to a rate of acceleration during the second time period to cause the flow of liquid into the pump during a refilling cycle portion to be substantially equal to the flow of liquid out of the pump during the pumping cycle portion and to cause pressure in the liquid flowing from the pump over a long time period to remain constant so that the pressure related variation is avoided;
    first means for forming a first signal;
    second means for forming a second signal;
    said second means for forming said second signal having a first input, a second input and an output;
    a high-pressure pump having an inlet port;
    said high-pressure pump being driven by said pump motor means;
    means for applying positive feedback to said pump motor means;
    said output being electrically connected to said means for applying positive feedback;
    said first input being electrically connected to a means for generating a signal proportional to a flow rate error of the liquid during a delivery stroke of said pump;
    said second input being electrically connected to an adjustable means for generating an increasing signal; and
    said adjustable means being adjusted to a value that causes said high-pressure pump during a period of time that starts substantially at the beginning of a refill stroke to cause liquid to flow through said inlet port of said high-pressure pump at a rate that does not cause cavitation.

2. A liquid chromatographic system in accordance with claim 1, in which:
    said liquid chromatographic system further includes a power means;
    said power means including a pulse-width modulator having a first input from said means for generating a first signal and a second input from said means for generating a second positive feedback signal;
    said liquid chromatographic system further includes a means for generating a negative feedback signal;
    said means for generating a negative feedback signal including means for feeding back a velocity signal during at least a portion of the pumping cycle, whereby delivery rate is constant during said portion.

3. A liquid chromatographic system in accordance with claim 2 in which:
    said first input to said pulse-width modulator establishes a first level linearly related to an error from a preset flow rate during a delivery stroke of the pump;
    said first signal during refill being changed to a second level proportional to said first level;
    said second input signal being a ramp signal related to velocity feedback.

4. A chromatographic system in accordance with claim 3 further including means for starting a refill cycle; said means for starting a refill cycle being electrically connected to a negative velocity feedback means.

5. A chromatographic system in accordance with claim 4 further including a first compensation circuit electrically connected in circuit with said means for starting a refill cycle and a first velocity negative feedback control circuit.

6. A liquid chromatographic system in accordance with claim 5 further including:
    means for generating a signal indicating motor speed;
    said means for generating a signal indicating motor speed being electrically connected to said first negative velocity feedback circuit means.

7. A liquid chromatographic system in accordance with claim 6 in which:
    the means for driving the motor includes said pulse-width modulator and means for supplying power to a motor;
    said pulse-width modulator being a comparator having its output electrically connected to the means for supplying power to a motor and having first and second input terminals;
    said output of said pulse-width modulator being electrically connected to said means for supplying power to a motor, whereby said pulse-width modulator supplies pulse-width modulated pulses to said means for supplying power to a motor; and
    said comparator including means for generating pulse-width-modulated pulses inversely related in width to the steepness of said ramp signal applied to a conductor and directly related to the amplitude of the signal applied to the first input of the pulse-width modulator, whereby said means for driving said motor provides pulses to maintain a constant speed in one mode and to provide constant acceleration in another mode.

8. A liquid chromatograph in accordance with claim 7 in which:
said liquid chromatograph furhter includes a first means for applying a first signal to said comparator and a second means for applying a second signal to said comparator;
said first means for applying a first signal to said comparator including means for applying said first signal during a pumping mode which varies in amplitude with deviations from a preset velocity; and
said second means for applying a second signal to said comparator including means for applying a periodic ramp, whereby said pulse-width modulator provides a pulse the width of which is directly related to the comparison between said first signal and said second signal so that the pulse width varies linearly in width with deviations from said preset pulse width.

9. A liquid chromatograph in accordance with claim 8 in which said second signal varies in rate of rise in accordance with a preset acceleration signal, whereby the pulse width of the pulse from said pulse-width modulator increases at a preset rate so as to provide acceleration of said pump motor.

10. A liquid chromatographic system in accordance with claim 9 including feedback means having a tachometer means for applying an output signal proportional to the velocity of said motor; said feedback means including a frequency-to-voltage converter.

11. A liquid chromatograph in accordance with claim 10 in which said frequency-to-voltage converter includes means for adjusting the amplitude of said signal related to the rate of pumping of said motor, whereby said flow rate may be adjusted to avoid cavitation.

12. A liquid chromatograph in accordance with claim 11 in which:
said liquid chromatograph further includes a nonlinear control system;
said nonlinear control system including means for generating periodic timing signals;
said means for generating periodic signals being electrically connected to said means for generating a ramp signal, whereby the timing of said ramp signal is controlled.

13. A liquid chromatographic system in accordance with claim 12 in which:
said liquid chromatograph further includes a multivibrator;
said multivibrator including means for providing pulses to reset a ramp generator and to reset said means for driving a motor.

14. A liquid chromatograph in accordance with claim 13 in which said ramp generator is electrically connected to receive said signal indicating pump speed and includes amplifier means for amplifying said signal indicating pump speed nonlinearly, whereby a ramp is provided which increases at a rate related to the rate of pumping.

15. A liquid chromatograph in accordance with claim 14 further including a capacitor electrically connected to the output of said amplifier and a switch means electrically connected across said capacitor; said switch means being adapted to receive signals from said multivibrator, whereby said ramp may be terminated and a new ramp started by discharging said capacitor.

16. A liquid chromatograph in accordance with claim 15 in which said negative velocity feedback circuit includes:
means for summing a current representing a preset pumping rate and a current representing the instantaneous velocity;
switch means electrically connected between said means for summing and said means for supplying power to said motor; and
means for activating said switch means to open said switch means upon receiving a refill cycle signal and closing said switch means a time after the start of a refill cycle related to said preset velocity.

17. A liquid chromatograph in accordance with claim 16 in which:
said liquid chromatograph further includes means for applying velocity feedback to said means for summing;
said means for applying velocity feedback to said means for summing including a compensating circuit electrically connected to receive velocity input and to apply a signal corrected for speed range to said means for summing.

18. A liquid chromatograph in accordance with claim 17 including:
first and second circuits for controlling acceleration of the pump motor in a time period starting with refill and terminating after fluid has been replaced;
said first means being a means for controlling the time duration of acceleration;
said first and second means being related to provide a sufficient amount of fluid while maintaining the rate of acceleration at a level which avoids cavitation.

19. A liquid chromatograph in accordance with claim 18 in which one of said first and second means has its amplitude adjusted by the rate of flow of said fluid prior to the refill cycle;
said means including a sample and hold circuit for storing a signal related to the speed of the pump prior to the refill cycle; and
said rate of acceleration being calibrated by an adjustment so that it does not exceed a rate which causes cavitation.

20. A liquid chromatograph in accordance with claim 19 in which said first means is a means for controlling the time duration of acceleration and said sample and hold circuit provides a potential to control the termination of the duration of the period of acceleration through a timer.

21. A liquid chromatograph in accordance with claim 20 in which the time duration of acceleration is controlled by a monostable multivibrator and a capacitor;
said capacitor being electrically connected to receive a signal from a sample and hold circuit indicating the flow rate of said pump during a delivery stroke.

22. A liquid chromatograph in accordance with claim 21 including:
a source of potential related to the speed of the pump motor during delivery;
means for controlling said first signal and said second signal in relation to said source of potential;
said first signal being used during at least a portion of said delivery stroke to maintain the rate of pumping constant; and said second signal being used as a factor to determine the rate of acceleration of said pump motor during a time period starting with the beginning of a refill cycle and extending for a time duration related to the rate of pumping prior to the start of the refill cycle.

23. A liquid chromatograph in accordance with claim 22 including a feedback signal from a tachometer related to the rate of pumping of said motor; and
said feedback signal being connected to said negative velocity feedback circuit and to said ramp circuit, whereby a feedback signal aids in control of the motor.

24. A liquid chromatographic system in accordance with claim 1 further including:
means for feeding back a velocity signal as a negative feedback signal during at least a portion of the pumping cycle, whereby delivery rate is constant during said portion; and
said positive feedback and negative feedback signal representing motor speed.

* * * * *